(12) United States Patent  
Yturralde et al.

(10) Patent No.: US 9,989,999 B2  
(45) Date of Patent: Jun. 5, 2018

(54) METHOD OF SCANNING CODES AND PROCESSING DATA WITH HANDHELD SCANNING JACKET

(71) Applicant: PATIENTSAFE SOLUTIONS, INC., San Diego, CA (US)

(72) Inventors: Mark C. Yturralde, San Diego, CA (US); Reza A. Ghanbari, San Diego, CA (US)

(73) Assignee: PatientSafe Solutions, Inc., San Diego, CA (US)

(*) Notice: Subject to any disclaimer, the term of this patent is extended or adjusted under 35 U.S.C. 154(b) by 1040 days.

(21) Appl. No.: 14/231,701

(22) Filed: Mar. 31, 2014

(65) Prior Publication Data

US 2014/0291394 A1 Oct. 2, 2014

Related U.S. Application Data

(63) Continuation of application No. 13/433,696, filed on Mar. 29, 2012, now Pat. No. 8,687,351, which is a continuation-in-part of application No. 29/416,709, filed on Mar. 26, 2012, now Pat. No. Des. 717,304.

(60) Provisional application No. 61/470,305, filed on Mar. 31, 2011.

(51) Int. Cl.
*G06F 1/16* (2006.01)
*G06Q 50/22* (2018.01)
*G06Q 50/24* (2012.01)

(52) U.S. Cl.
CPC .......... *G06F 1/1632* (2013.01); *G06F 1/1628* (2013.01); *G06Q 50/22* (2013.01); *G06Q 50/24* (2013.01)

(58) Field of Classification Search
CPC ................ G06F 1/1628; G06F 1/1632; G06Q 50/22–50/24

See application file for complete search history.

(56) References Cited

U.S. PATENT DOCUMENTS

| | | | |
|---|---|---|---|
| 4,916,441 | A | 4/1990 | Gombrich |
| D322,165 | S | 12/1991 | Lloyd |
| 5,360,108 | A | 11/1994 | Alagia |
| 5,368,159 | A | 11/1994 | Doria |
| 5,388,692 | A | 2/1995 | Withrow et al. |
| 5,583,742 | A | 12/1996 | Noda et al. |
| D379,265 | S | 5/1997 | Wathen et al. |
| 5,805,416 | A | 9/1998 | Friend et al. |
| 5,996,956 | A | 12/1999 | Shawver |

(Continued)

OTHER PUBLICATIONS

International Search Report and Written Opinion issued by the International Searching Authority for Application No. PCT/US2013/034619, dated Jul. 26, 2013, 9 pages.

*Primary Examiner* — Robert A Sorey

(57) ABSTRACT

A method of reading codes with a reader mounted at least partially within a jacket and communicating the read codes to a handheld device also mounted at least partially within the jacket. The codes may identify a medicine, identify a patient, run an inventory, run a patient safety application, or other process control application located on the handheld device. The jacket includes an opening configured to align and engage with a display surface of the handheld device to simultaneously display being read. The jacket is portable and small and light enough to be carried by a user while working in a healthcare facility.

17 Claims, 21 Drawing Sheets

(56) References Cited

U.S. PATENT DOCUMENTS

| | | |
|---|---|---|
| D424,035 S | 5/2000 | Steiner et al. |
| 6,064,779 A | 5/2000 | Neukermans et al. |
| 6,108,197 A | 8/2000 | Janik et al. |
| 6,188,917 B1 * | 2/2001 | Laureanti .......... H04M 1/72527 379/38 |
| 6,201,867 B1 | 3/2001 | Koike |
| 6,744,537 B1 | 6/2004 | Chiba et al. |
| 6,789,734 B1 | 9/2004 | Tu |
| 6,842,652 B2 | 1/2005 | Yeung |
| 6,886,749 B2 | 5/2005 | Chiba et al. |
| 6,963,756 B2 | 11/2005 | Lubowicki et al. |
| 6,995,976 B2 | 2/2006 | Richardson |
| 7,050,712 B2 | 5/2006 | Shimamura |
| 7,158,376 B2 | 1/2007 | Richardson et al. |
| 7,180,735 B2 | 2/2007 | Thomas et al. |
| 7,312,984 B2 | 12/2007 | Richardson et al. |
| D563,093 S | 3/2008 | Nussberger et al. |
| D565,291 S | 4/2008 | Brandenburg et al. |
| D582,149 S | 12/2008 | Tan |
| D593,319 S | 6/2009 | Richardson et al. |
| D593,746 S | 6/2009 | Richardson et al. |
| 7,555,325 B2 | 6/2009 | Goros |
| D597,067 S | 7/2009 | Oh et al. |
| 7,594,576 B2 | 9/2009 | Chen et al. |
| 7,609,512 B2 | 10/2009 | Richardson et al. |
| D603,602 S | 11/2009 | Richardson et al. |
| 7,612,997 B1 | 11/2009 | Diebel et al. |
| D605,850 S | 12/2009 | Richardson et al. |
| D606,305 S | 12/2009 | Lee et al. |
| D606,751 S | 12/2009 | Andre et al. |
| D609,463 S | 2/2010 | Bullen |
| D610,568 S | 2/2010 | Yu |
| 7,663,878 B2 | 2/2010 | Swan et al. |
| 7,688,580 B2 | 3/2010 | Richardson et al. |
| D613,282 S | 4/2010 | Richardson et al. |
| D615,535 S | 5/2010 | Richardson et al. |
| D617,784 S | 6/2010 | Richardson et al. |
| D619,130 S | 7/2010 | Fellig |
| D619,574 S | 7/2010 | Richardson et al. |
| D623,179 S | 9/2010 | Richardson et al. |
| D624,064 S | 9/2010 | Esposito |
| D624,908 S | 10/2010 | Huskinson |
| D626,119 S | 10/2010 | Fellig |
| D628,994 S | 12/2010 | Griffin et al. |
| D629,784 S | 12/2010 | Forsyth |
| 7,859,222 B2 | 12/2010 | Woud |
| D632,685 S | 2/2011 | Richardson et al. |
| 7,889,498 B2 | 2/2011 | Diebel et al. |
| D635,131 S | 3/2011 | Roman |
| D636,386 S | 4/2011 | Richardson et al. |
| 7,933,122 B2 | 4/2011 | Richardson |
| D637,589 S | 5/2011 | Willes et al. |
| D638,411 S | 5/2011 | Willes et al. |
| D638,828 S | 5/2011 | Melanson et al. |
| D638,829 S | 5/2011 | Melanson et al. |
| D641,013 S | 7/2011 | Richardson et al. |
| D642,169 S | 7/2011 | Andre et al. |
| 7,984,804 B2 | 7/2011 | Lebauer |
| D643,424 S | 8/2011 | Richardson et al. |
| D644,218 S | 8/2011 | Akana et al. |
| D644,638 S | 9/2011 | Melanson et al. |
| D645,015 S | 9/2011 | Lee et al. |
| D645,031 S | 9/2011 | Richardson et al. |
| D646,671 S | 10/2011 | Fathollahi |
| D650,810 S | 12/2011 | Lemelman et al. |
| D651,203 S | 12/2011 | Michie et al. |
| D651,594 S | 1/2012 | Melanson et al. |
| D653,202 S | 1/2012 | Hasbrook et al. |
| D653,660 S | 2/2012 | Sweet |
| D654,894 S | 2/2012 | Kim |
| D656,495 S | 3/2012 | Andre et al. |
| D658,165 S | 4/2012 | Freeman |
| D658,166 S | 4/2012 | Bau |
| 8,170,632 B2 | 5/2012 | Hsu |
| 8,191,706 B1 | 6/2012 | Liu |
| 8,204,561 B2 | 6/2012 | Mongan et al. |
| D662,924 S | 7/2012 | Melanson et al. |
| D662,927 S | 7/2012 | Fahrendorff et al. |
| 8,245,842 B2 | 8/2012 | Bau |
| D667,783 S | 9/2012 | Zhang et al. |
| 8,286,789 B2 | 10/2012 | Wilson et al. |
| D670,278 S | 11/2012 | Hamann |
| D670,280 S | 11/2012 | Rayner |
| D670,281 S | 11/2012 | Corpuz et al. |
| D670,694 S | 11/2012 | Li |
| 8,302,769 B2 | 11/2012 | Justiss |
| D673,936 S | 1/2013 | Michie et al. |
| 8,342,325 B2 | 1/2013 | Rayner |
| D675,947 S | 2/2013 | Janky et al. |
| D676,032 S | 2/2013 | Stump et al. |
| D677,251 S | 3/2013 | Melanson et al. |
| 8,395,894 B2 | 3/2013 | Richardson et al. |
| D679,270 S | 4/2013 | Eicher |
| D679,684 S | 4/2013 | Baker et al. |
| D681,020 S | 4/2013 | Magness et al. |
| 8,430,240 B2 | 4/2013 | Kim |
| D681,613 S | 5/2013 | Magness et al. |
| D681,619 S | 5/2013 | Smith |
| D683,338 S | 5/2013 | Wilson et al. |
| 8,439,191 B1 | 5/2013 | Lu |
| 8,457,701 B2 | 6/2013 | Diebel |
| D685,754 S | 7/2013 | Palmer et al. |
| 8,483,758 B2 | 7/2013 | Huang |
| D688,234 S | 8/2013 | Esses |
| D689,475 S | 9/2013 | Andre et al. |
| 8,523,068 B2 | 9/2013 | Hsu et al. |
| 8,526,180 B2 | 9/2013 | Rayner |
| 8,531,824 B2 | 9/2013 | Rayner |
| 8,531,833 B2 | 9/2013 | Diebel et al. |
| D691,990 S | 10/2013 | Rayner |
| D692,419 S | 10/2013 | Rayner |
| 8,548,541 B2 | 10/2013 | Rayner |
| 8,564,950 B2 | 10/2013 | Rayner |
| 8,570,737 B2 | 10/2013 | Rayner |
| D692,878 S | 11/2013 | Akana et al. |
| D692,893 S | 11/2013 | Wesolek |
| D694,227 S | 11/2013 | Rayner |
| 8,584,847 B2 | 11/2013 | Tages et al. |
| D695,730 S | 12/2013 | Wicks et al. |
| D696,234 S | 12/2013 | Wright |
| 8,599,547 B2 | 12/2013 | Richardson et al. |
| 8,623,494 B2 | 1/2014 | Richardson et al. |
| 8,644,011 B2 | 2/2014 | Parkinson |
| D702,221 S | 4/2014 | Vandiver |
| D703,199 S | 4/2014 | Smith |
| D703,652 S | 4/2014 | Melanson et al. |
| 8,687,351 B2 | 4/2014 | Yturralde et al. |
| 8,708,142 B2 | 4/2014 | Rayner |
| D704,182 S | 5/2014 | Smith |
| D705,763 S | 5/2014 | Fastman et al. |
| D705,768 S | 5/2014 | Melanson et al. |
| D705,769 S | 5/2014 | Esses |
| 8,716,598 B2 | 5/2014 | Pan |
| 8,735,721 B2 | 5/2014 | Pan |
| D706,253 S | 6/2014 | Simmer |
| 8,767,385 B2 | 7/2014 | Richardson et al. |
| 8,774,446 B2 | 7/2014 | Merenda |
| D717,304 S | 11/2014 | Yturralde et al. |
| 2002/0126440 A1 | 9/2002 | Webb et al. |
| 2002/0137475 A1 | 9/2002 | Shou et al. |
| 2002/0148745 A1 | 10/2002 | Chang |
| 2002/0172017 A1 * | 11/2002 | Tarnowski ............ G06F 1/1622 361/730 |
| 2003/0024991 A1 | 2/2003 | Tuli |
| 2003/0062882 A1 | 4/2003 | Shih |
| 2003/0095374 A1 | 5/2003 | Richardson |
| 2003/0104850 A1 | 6/2003 | Lai et al. |
| 2003/0151780 A1 | 8/2003 | Tsai |
| 2003/0222150 A1 * | 12/2003 | Sato ...................... G06F 1/1626 235/472.02 |
| 2004/0089570 A1 | 5/2004 | Chien et al. |
| 2005/0174727 A1 | 8/2005 | Thomas et al. |
| 2005/0184153 A1 * | 8/2005 | Auchinleck ........... G06F 19/327 235/385 |

(56) References Cited

U.S. PATENT DOCUMENTS

| | | |
|---|---|---|
| 2005/0237582 A1* | 10/2005 | Hamilton ............ G06K 7/10881 358/474 |
| 2006/0104021 A1 | 5/2006 | Chen et al. |
| 2006/0105722 A1* | 5/2006 | Kumar ................. G06F 1/1632 455/90.3 |
| 2006/0163360 A1 | 7/2006 | Steusloff et al. |
| 2006/0274493 A1* | 12/2006 | Richardson .......... G06F 1/1626 361/679.4 |
| 2007/0049365 A1 | 3/2007 | Norris |
| 2007/0110416 A1 | 5/2007 | Yamaguchi et al. |
| 2007/0139873 A1 | 6/2007 | Thomas et al. |
| 2007/0146985 A1 | 6/2007 | Mick et al. |
| 2007/0179348 A1 | 8/2007 | Shen |
| 2007/0223183 A1 | 9/2007 | Oja |
| 2007/0297149 A1 | 12/2007 | Richardson et al. |
| 2008/0053851 A1 | 3/2008 | Ko et al. |
| 2008/0251512 A1 | 10/2008 | Griffin et al. |
| 2008/0316687 A1 | 12/2008 | Richardson et al. |
| 2009/0001171 A1* | 1/2009 | Carlson .............. G06K 7/10554 235/462.41 |
| 2009/0009945 A1 | 1/2009 | Johnson et al. |
| 2009/0036181 A1 | 2/2009 | Lee |
| 2009/0114556 A1 | 5/2009 | Tai et al. |
| 2009/0215412 A1 | 8/2009 | Liu et al. |
| 2009/0245565 A1 | 10/2009 | Mittleman et al. |
| 2009/0247244 A1 | 10/2009 | Mittleman et al. |
| 2009/0257189 A1 | 10/2009 | Wang et al. |
| 2010/0008028 A1 | 1/2010 | Richardson et al. |
| 2010/0048257 A1 | 2/2010 | Prest et al. |
| 2010/0048267 A1 | 2/2010 | Lin |
| 2010/0085691 A1 | 4/2010 | Yeh et al. |
| 2010/0096284 A1 | 4/2010 | Bau |
| 2010/0104814 A1 | 4/2010 | Richardson et al. |
| 2010/0122756 A1 | 5/2010 | Longinotti-Buitoni |
| 2010/0124040 A1 | 5/2010 | Diebel et al. |
| 2010/0203931 A1 | 8/2010 | Hynecek et al. |
| 2010/0238119 A1 | 9/2010 | Dubrovsky et al. |
| 2011/0003624 A1 | 1/2011 | Jung et al. |
| 2011/0073505 A1 | 3/2011 | Stiehl |
| 2011/0117969 A1 | 5/2011 | Hanson |
| 2011/0183721 A1 | 7/2011 | Hill et al. |
| 2011/0192510 A1 | 8/2011 | Bau |
| 2011/0253569 A1 | 10/2011 | Lord |
| 2012/0018323 A1 | 1/2012 | Johnson et al. |
| 2012/0018325 A1 | 1/2012 | Kim |
| 2012/0031788 A1 | 2/2012 | Mongan et al. |
| 2012/0037524 A1 | 2/2012 | Lonsdale et al. |
| 2012/0043235 A1 | 2/2012 | Klement |
| 2012/0056789 A1 | 3/2012 | Sohn |
| 2012/0074005 A1 | 3/2012 | Johnson et al. |
| 2012/0118772 A1 | 5/2012 | Ellis-Brown |
| 2012/0118773 A1 | 5/2012 | Rayner |
| 2012/0168336 A1 | 7/2012 | Schmidt et al. |
| 2012/0178506 A1 | 7/2012 | Sorias et al. |
| 2012/0211382 A1 | 8/2012 | Rayner |
| 2012/0229843 A1 | 9/2012 | Golle et al. |
| 2012/0285847 A1 | 11/2012 | Olsson et al. |
| 2012/0305422 A1 | 12/2012 | Vandiver |
| 2012/0320503 A1 | 12/2012 | Yturralde et al. |
| 2013/0029790 A1 | 1/2013 | Clark |
| 2013/0092576 A1 | 4/2013 | Rayner |
| 2013/0113348 A1 | 5/2013 | Holben et al. |
| 2013/0146491 A1 | 6/2013 | Ghali et al. |
| 2013/0148295 A1 | 6/2013 | Minn et al. |
| 2013/0157730 A1 | 6/2013 | McCormac et al. |
| 2013/0175186 A1 | 7/2013 | Simmer |
| 2013/0206621 A1 | 8/2013 | Bau |
| 2013/0292281 A1 | 11/2013 | Chung |
| 2013/0341222 A1 | 12/2013 | Lin |
| 2014/0034531 A1 | 2/2014 | Wang |
| 2014/0043441 A1 | 2/2014 | Borenstein et al. |
| 2014/0043442 A1 | 2/2014 | Borenstein et al. |
| 2014/0076753 A1 | 3/2014 | Limber et al. |
| 2014/0085777 A1 | 3/2014 | Yeh et al. |
| 2014/0092532 A1 | 4/2014 | Kole et al. |
| 2014/0092537 A1 | 4/2014 | Bae et al. |
| 2014/0098476 A1 | 4/2014 | Severson et al. |
| 2014/0104761 A1 | 4/2014 | Hsu |
| 2014/0104765 A1 | 4/2014 | Hoshino |
| 2014/0111910 A1 | 4/2014 | Lin et al. |
| 2014/0111913 A1 | 4/2014 | Liu et al. |
| 2014/0118905 A1 | 5/2014 | Chung et al. |
| 2014/0139978 A1 | 5/2014 | Kwong |
| 2014/0146441 A1 | 5/2014 | Hautamaki et al. |
| 2014/0160650 A1 | 6/2014 | Stevens et al. |
| 2014/0168212 A1 | 6/2014 | Jones |
| 2014/0168867 A1 | 6/2014 | Choi et al. |
| 2014/0168870 A1 | 6/2014 | Cho et al. |
| 2014/0185206 A1 | 7/2014 | Kim et al. |
| 2014/0192459 A1 | 7/2014 | Kwong et al. |
| 2014/0192462 A1 | 7/2014 | Park |

* cited by examiner

METHOD OF SCANNING CODES AND PROCESSING DATA WITH HANDHELD SCANNING JACKET

RELATED APPLICATIONS

This application is a continuation of U.S. application Ser. No. 13/433,696, filed Mar. 29, 2012, now U.S. Pat. No. 8,687,351, which is a continuation-in-part of U.S. Design patent application No. 29/416,709, filed on Mar. 26, 2012, entitled JACKET FOR A HANDHELD DEVICE, and which also claims the benefit of U.S. Provisional Application No. 61/470,305 entitled SCANNING JACKET FOR A HANDHELD DEVICE, filed on Mar. 31, 2011, the entire contents of each of these prior applications are incorporated herein by reference.

BACKGROUND

Field of the Disclosure

This application generally relates to a jacket for a handheld device. More particularly, this application relates to a jacket including an optical scanner positioned to allow a user to view a display on the handheld device while performing a task, for example, while scanning an item.

Description of the Related Technology

Some computing tasks or environments require a high degree of mobility, ease of operation, and low cost implementation due to a large number of users. One example of such a task is the administration and documentation of care provided to patients in a healthcare or hospital environment. Computer resources in these environments are limited due to inadequate availability of access points such as input/output (I/O) stations or terminals. Although stationary terminals may have a large screen, familiar full-featured keyboard, and mouse input devices, such terminals can be inconvenient to use in certain environments due to lack of portability, and/or availability due to cost and space constraints. Notebook computers with wireless communication capabilities can increase the convenience of computer terminals while maintaining relatively fast and available computing power. However, they are still somewhat large in size, bulky to transport, have limited battery life, require two hands to operate, are expensive, and/or can be damaged by exposure to liquids and/or solid particles (for example, dust or other debris).

A plurality of small sized wireless computing devices have been developed, such as wireless personal digital assistants (PDA's), for use by caregivers in administration and documentation of medical care. For example, U.S. Pat. No. 4,916,441 to Gombrich describes a handheld terminal that includes a wireless transmitter and a bar code scanner for entering medical data into a computer system. Unfortunately, a healthcare professional needs to manually type much of the information onto a small keyboard on the device. This is inconvenient and time-consuming in a healthcare environment. Further, this device is susceptible to damage caused by exposure to liquids and/or solid particles present in healthcare environments.

SUMMARY OF CERTAIN INVENTIVE ASPECTS

In one aspect, a jacket for a handheld device is disclosed. The jacket may include, for example, a housing, a connecter member disposed at least partially within the housing, and a scanner disposed at least partially within the housing. In some embodiments, the housing defines a receiving area for the handheld device and includes an opening configured to align with a display surface of the handheld device and engaging structure disposed about the opening. The engaging structure may be configured to circumferentially engage at least a portion of the display surface of the handheld device when the handheld device is disposed within the receiving area. In some embodiments, the connector member is configured to connect to the handheld device when the handheld device is disposed within the receiving area. In some embodiments, the scanner is configured to communicate with the handheld device or an application on the handheld device at least when the handheld device is connected to the connector member.

In another aspect, a method of forming a handheld terminal includes, for example, providing a handheld device having a display surface, providing a jacket including a housing which defines a receiving area, and disposing the handheld device within the receiving area of the housing. In some embodiments, the housing includes an opening configured to align with the display surface of the handheld device and engaging structure disposed circumferentially about the opening. In some embodiments, the jacket also includes a connector member and a scanner disposed at least partially within the housing.

In another aspect, a method of performing a task in a healthcare environment includes providing a handheld terminal including a jacket and a handheld device. In some embodiments, the jacket includes a housing including a receiving area and at least one opening. In some embodiments, the jacket also includes a connector member disposed at least partially within the housing and a scanner disposed at least partially within the housing. In some embodiments, the handheld device is disposed within the receiving area of the housing and includes a display surface that is aligned with the at least one opening of the housing and that contacts the housing along a boundary of a portion of the display surface to seal a portion of the receiving area disposed below the display surface. In some embodiments, the method may also include scanning an object while holding the handheld terminal and viewing the display surface through the at least one opening.

In another aspect, a scanning jacket includes, for example, a first portion adapted to house a handheld device, a second portion adapted to house a scanner, and a scanner housed at least partially within the second portion. In some embodiments, the first portion includes a window or screen that can be aligned with a display portion of the handheld device. In some embodiments, the scanner can be disposed at an angle with respect to the first side of the jacket. In some embodiments, the scanner can communicate with the handheld device (or with an application installed on the handheld device) to allow use of the handheld device as a scanner. In some embodiments, the jacket and its components can be watertight and drop resistant, allowing use in harsh environments such as healthcare settings.

In another aspect, a jacket for a handheld device includes, for example, a housing defining a receiving area for the handheld device, and a connector member disposed at least partially within the housing.

In some embodiments, the housing includes an opening configured to align with a display surface of the handheld device, and an engaging structure disposed about the opening, the engaging structure configured to circumferentially engage a portion of the display surface of the handheld device when the handheld device is disposed within the receiving area. In some embodiments, the connector member is configured to electrically connect to the handheld device when the handheld device is disposed within the receiving area.

In some embodiments, the jacket further includes a scanner disposed at least partially within the housing, the scanner configured to communicate with the handheld device or an application on the handheld device at least when the handheld device is connected to the connector member. In some embodiments, the housing and display surface seal a portion of the receiving area disposed below the display surface when the handheld device is connected to the connector member. In some embodiments, the display surface is physically accessible through the opening when the handheld device is connected to the connector member. In some embodiments, the engaging structure includes a gasket. In some embodiments, the jacket further includes a battery. In some embodiments, the battery is electrically connected to the scanner. In some embodiments, the battery is electrically connected to the handheld device at least when the handheld device is connected to the connector member.

In some embodiments, the housing includes a first cover and a second cover. In some embodiments, the second cover includes a first transparent window aligned with the scanner. In some embodiments, the first transparent window is disposed on a surface of the jacket opposite the opening. In some embodiments, the first transparent window is disposed at an angle with respect to a plane of the jacket. In some embodiments, the first transparent window is disposed at an angle between about 79° and 80.5° with respect to a plane of the jacket. In some embodiments, the jacket further includes a scan button configured to control the scanner. In some embodiments, the opening, first transparent window, and scan button are configured such that a user may simultaneously perform the following tasks: hold the jacket with a single hand; contact the scan button with a thumb of the single hand; view at least a portion of the display surface of the handheld device through the opening; view an object to be scanned; and scan the object to be scanned with the scanner. In some embodiments, the second cover includes a second transparent window aligned with a camera of the handheld device when the handheld device is connected to the connector member.

In some embodiments, the opening is disposed in the first cover. In some embodiments, the first cover includes at least one transparent window configured to align with a camera of the handheld device when the handheld device is disposed within the receiving area. In some embodiments, the second cover includes a contact portion sized and shaped to contact the inner portion of a hand of a user. In some embodiments, the contact portion includes a material that is different from a material of at least one other portion of the second cover. In some embodiments, the jacket further includes a speaker configured to communicate with the handheld device at least when the handheld device is connected to the connector member. In some embodiments, the jacket further includes a microphone configured to communicate with the handheld device at least when the handheld device is connected to the connector member. In some embodiments, the jacket further includes a vibrating element configured to communicate with the handheld device at least when the handheld device is connected to the connector member. In some embodiments, the housing includes one or more pass-through buttons. In some embodiments, the housing includes a polycarbonate material.

In another aspect, a jacket for a handheld device includes, for example, a housing defining a receiving area for the handheld device, the housing including an opening configured to align with a display surface of the handheld device, a connector member disposed at least partially within the housing, the connector member configured to electrically connect to the handheld device when the handheld device is disposed within the receiving area, and a scanner disposed at least partially within the housing, the scanner configured to communicate with the handheld device or an application on the handheld device when the handheld device is connected to the connector member.

In some embodiments, the housing includes a first transparent window disposed on a surface of the jacket opposite the opening. In some embodiments, the first transparent window is aligned with the scanner at an angle between about 70° and 90° with respect to a plane of the jacket. In some embodiments, the first transparent window is aligned with the scanner at an angle between about 75° and 85° with respect to a plane of the jacket. In some embodiments, the first transparent window is aligned with the scanner at an angle between about 79° and 81° with respect to a plane of the jacket.

In another aspect, a jacket for a handheld device is provided. The jacket includes, for example, a housing formed of a polycarbonate, polycarbamate, polyurethane, or acrylonitrile butadiene styrene material the housing defining a receiving area for the handheld device, the housing including a first cover and a second cover, the first cover including an opening configured to align with a display surface of the handheld device, and a gasket disposed about the opening and the configured to circumferentially engage a portion of the display surface of the handheld device when the handheld device is disposed within the receiving area, and a connector member disposed at least partially within the housing, the connector member configured to electrically connect to the handheld device when the handheld device is disposed within the receiving area. In some embodiments, the housing and display surface seal a portion of the receiving area disposed below the display surface when the handheld device is connected to the connector member. In some embodiments, the display surface is physically accessible through the opening when the handheld device is connected to the connector member.

In another aspect, a system is provided having a jacket electrically connected to and housing a handheld device. In some embodiments, the system is configured to facilitate workflow in a medical environment. In some embodiments the medical environment is a hospital.

In another aspect, a method of forming a handheld terminal includes, for example, providing a handheld device having a display surface, providing a jacket including a housing defining a receiving area for the handheld device, the housing having an opening configured to align with the display surface of the handheld device, an engaging structure disposed circumferentially about the opening, a connector member disposed at least partially within the housing, and a scanner disposed at least partially within the housing, and disposing the handheld device within the receiving area of the housing.

In some embodiments, the method further includes circumferentially engaging at least a portion of the display surface of the handheld device with the engaging structure of the housing. In some embodiments, circumferentially engaging at least a portion of the display surface of the handheld device with the engaging structure includes sealing a portion of the receiving area disposed below the display surface. In some embodiments, the method further includes connecting the handheld device to the connector member. In some embodiments, connecting the handheld device to the connector member includes connecting the handheld device or an application on the handheld device with the scanner.

In another aspect, a method of performing a task in a healthcare environment includes, for example, providing a handheld terminal with a jacket including a housing having a receiving space and at least one opening, a connector member disposed at least partially within the housing, and a scanner disposed at least partially within the housing, and a handheld device disposed within the receiving space of the housing, the handheld device including a display surface aligned with the at least one opening of the housing and that contacts the housing along a boundary of a portion of the display surface to seal a portion of the receiving area disposed below the display surface, and scanning an object while holding the handheld terminal and viewing the display surface through the at least one opening.

In some embodiments, the method further includes contacting the display surface through the at least one opening. In some embodiments, scanning the object includes receiving an input from an input from a scanning button of the jacket. In some embodiments, the jacket is resistant to liquid cleaning agents. In some embodiments, scanning the object and viewing the display surface occur simultaneously.

BRIEF DESCRIPTION OF THE DRAWINGS

The above-mentioned and other features will now be described with reference to the drawings of various embodiments which are intended to illustrate but not to limit the invention. An apparatus, system or method according to some of the described embodiments can have several aspects, no single one of which necessarily is solely responsible for the desirable attributes of the apparatus, system or method. After considering this discussion, and particularly after reading the section entitled "Detailed Description of Certain Inventive Embodiments" one will understand how illustrated features serve to explain certain principles of the present disclosure. The drawings contain the following figures.

DETAILED DESCRIPTION OF CERTAIN INVENTIVE EMBODIMENTS

Figure 1A:
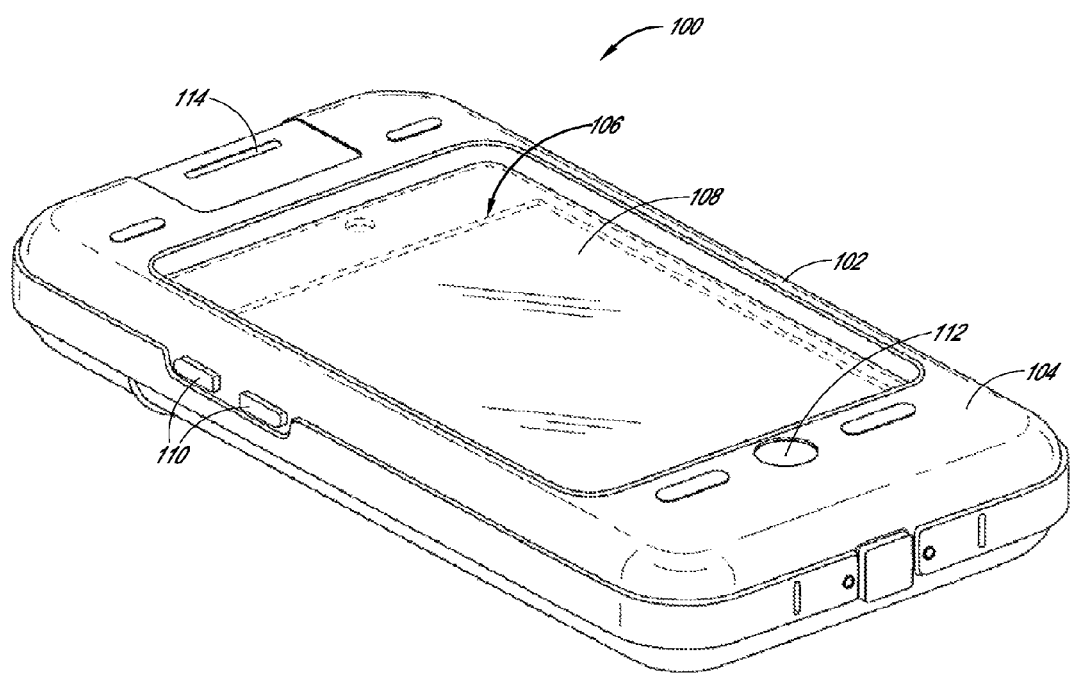
FIG. 1A shows a perspective view of a jacket 100 according to an embodiment.

In the following detailed description, only certain exemplary embodiments of the present disclosure have been shown and described, simply by way of illustration. As those skilled in the art would realize, the described embodiments may be modified in various different ways, all without departing from the spirit or scope of the present disclosure. Accordingly, the drawings and description are to be regarded as illustrative in nature and not restrictive. In addition, when an element is referred to as being "on" another element, it can be directly on the another element or be indirectly on the another element with one or more intervening elements interposed therebetween. Also, when an element is referred to as being "connected to" another element, it can be directly connected to the another element or be indirectly connected to the another element with one or more intervening elements interposed therebetween. Hereinafter, like reference numerals refer to like elements.

As noted above, the teachings herein can be applied in a multitude of different ways. For example, although the illustrated embodiments are configured for use with a non-cellular handheld device, for example, an iPod Touch®, embodiments can be configured for use with a variety of other handheld electronic devices, including, but not limited to, cellular phones, smartphones (for example, an iPhone®), VoIP handsets, wireless devices, bluetooth devices, personal data assistants (PDAs), handheld or portable computers, netbooks, notebooks, smartbooks, tablets, and other portable electronic devices. Thus, the teachings are not intended to be limited to the implementations depicted solely in the figures, but instead have wide applicability as will be readily apparent to a person having ordinary skill in the art.

In embodiments of the disclosure, a jacket or housing structure is provided for at least partially housing or encasing a handheld electronic device. In this way, the jacket and the handheld electronic device can together form a handheld computing device and/or handheld terminal. The jacket may include a connector assembly configured to connect to and communicate with the handheld electronic device. The jacket also can optionally include a transparent screen configured to align with a display on the handheld electronic device, at least when the device is connected to and housed within the jacket. In some embodiments, the jacket does not include a transparent screen and can include a sealing structure configured to circumscribe and engage at least a portion of a screen, input surface, and/or display surface of a housed handheld electronic device. In this way, the jacket and handheld device can engage one another to form a seal or barrier configured to protect components of the jacket and/or handheld device disposed below the screen of the handheld device and within the jacket. For example, a seal formed between the jacket and the screen of the handheld device can protect electronic components of the handheld device and jacket from solid particles and/or liquids that the resultant terminal or computing device may be exposed to. Further, the engagement between the jacket and handheld device can provide an absorbing structure configured to absorb impactful forces that may be imposed on the jacket and/or handheld device to prevent these impactful forces from harming or adversely affecting the functionality of the resultant terminal. In this way, the absorbing structure can allow the jacket and handheld device to be used regularly in a working environment, for example, a hospital.

In some embodiments, the jacket further includes an optical scanner and a scanning engine that communicates with the handheld device and/or an application on the handheld device at least when the device is connected to the jacket. The scanner, or code reader, can be used to read codes corresponding to, for example, patient identification, item identification, documentation characters and phrases, commands, and instructions. The codes are preferably machine readable codes, including one and two dimensional optically readable codes such as bar codes, but can include radio frequency identification (RF ID) devices or tags. The codes can be applied to objects, cards, or placards throughout a healthcare environment. By such a configuration, embodiments disclosed herein can allow for the use of a handheld electronic device, such as an iPod Touch®, as an optical scanner (for example, a barcode scanner), adding to the capability of the handheld device. Embodiments can thus be used in various applications, including identification of medicines and patients, in healthcare workflow applications and other process control applications.

In some embodiments disclosed herein, the jacket can include a battery, for example, a lithium polymer battery, configured to provide power to the optical scanner, scanning engine, and/or handheld device. In some embodiments, the battery can supplement a battery provided with the handheld device. In this way, the battery can be configured to allow the handheld device and electronic components of the jacket to be used for an extended work shift, for example, for 12 or more continuous hours, without requiring a charge or a replacement battery.

In some embodiments, the jacket can be configured to be liquid-resistant, cleaning-agent resistant, and/or drop-resistant, so as to be usable in harsh environments such as, for example, a healthcare setting. For example, the jacket can include one or more resilient materials, for example, a resilient polycarbonate material. Such materials can be configured to absorb impactful forces present on the jacket without transferring such forces to internal electronic components. Further, such materials can withstand regular exposure to healthcare grade cleaning-agents without degrading. In this way, the jacket can be easily sanitized or cleaned. Additionally, as discussed below, the structures of the jacket and the handheld device can engage one another to create a seal to prevent the ingress of solid particles and/or liquids into an inner area of the jacket. In some embodiments, the jacket can include a microphone and speaker that communicate (for example, through the connector) with the handheld device. These structures can allow for the use of the handheld device (including a non-cellular device such as an iPod Touch®) as a verbal and aural communication device, such as, for example, a voice over internet protocol (VoIP) handset.

FIG. 1A shows a perspective view of a jacket 100 according to an embodiment. The jacket 100 is designed to fit ergonomically and/or comfortably in a single hand of a user. In some embodiments, to facilitate an ergonomic and/or comfortable grip, the jacket 100 can include rounded contours and/or surfaces such that a user's hand is not exposed to sharp edges and/or corners. Further, the jacket 100 can be formed of a soft resilient material, for example, a polycarbonate material. In addition to providing the function of an ergonomic and/or comfortable grip, the jacket 100 can be configured to be aesthetically pleasing to the eye, in some embodiments.

Still referring to FIG. 1A, the jacket 100 includes a front cover 102 and a back cover (not visible in FIG. 1A) which form part of a protective case 104. The jacket 100 includes a receiving area 106 (indicated with dashed lines) configured to receive a handheld device, such as an iPod Touch®. The front cover 102 includes a transparent screen 108 which is configured to align with a display on the handheld device. The transparent screen 108 can also be configured to allow a user to interact with a touchscreen or other input mechanism on the handheld device. The front cover 102, the back cover, and/or the case 104 can include one or more pass-through buttons, such as pass-through buttons 110 and 112, configured to align with input buttons on the device and allow a user to access the input buttons on the device through the jacket 100. In the illustrated embodiment, the buttons 110 are configured to align with volume control buttons on the handheld device and the button 112 is configured to align with a menu button on the handheld device. The jacket 100 can also include a speaker 114.

Figure 1B:
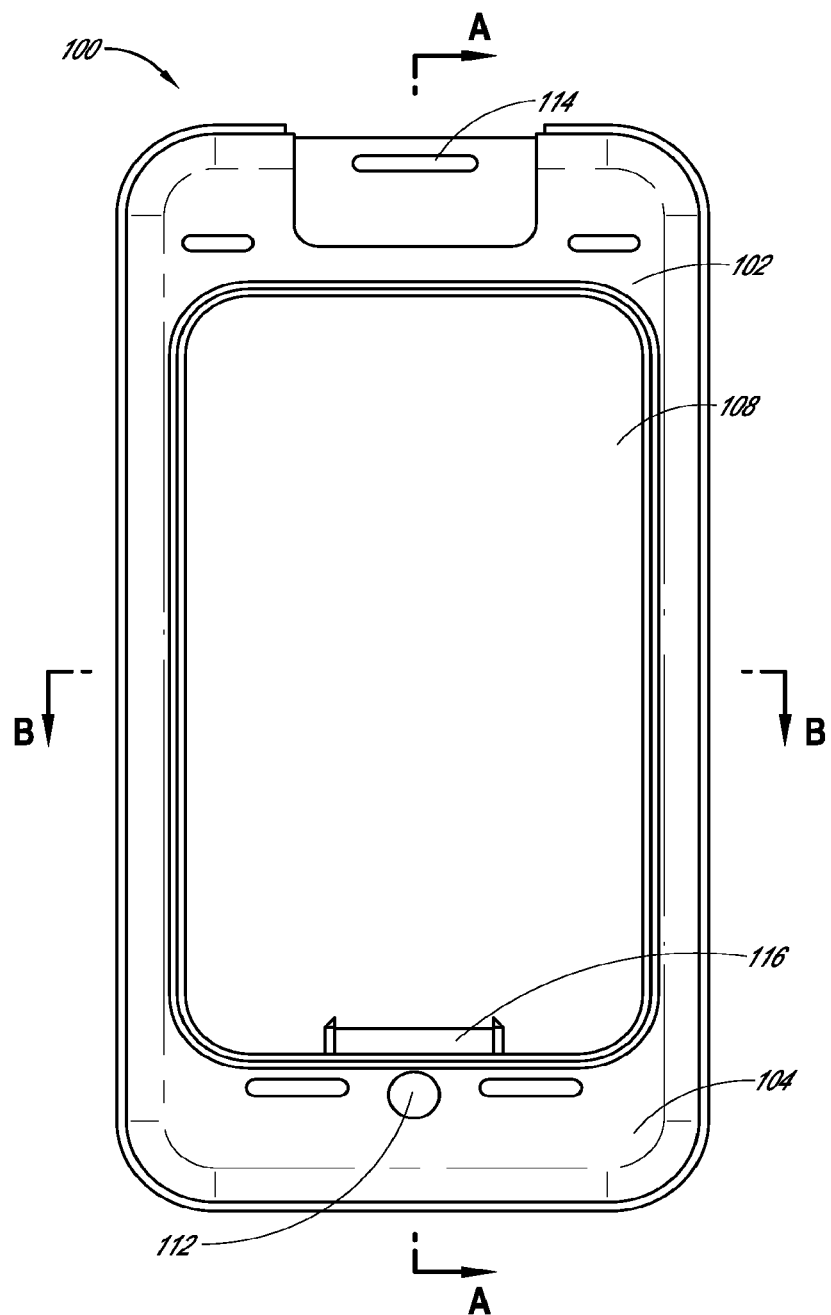
FIG. 1B shows a plan view of the front side of the jacket 100.
Figure 1C:
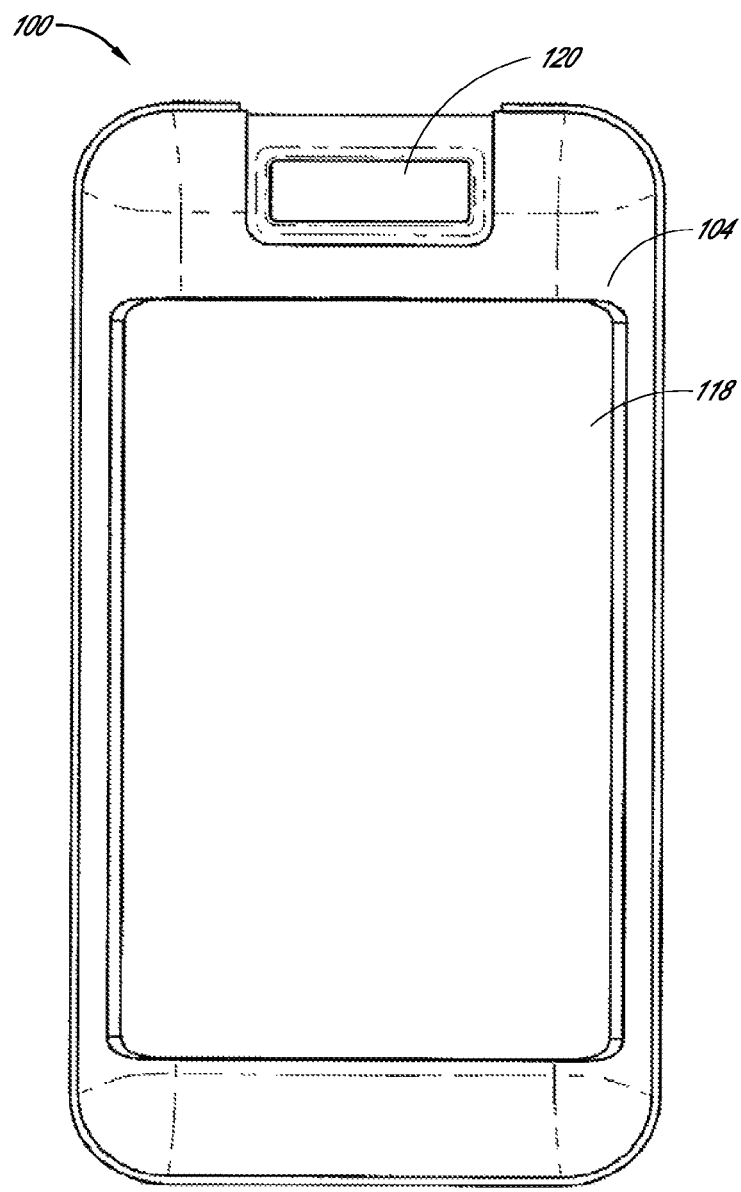
FIG. 1C shows a plan view of the back side of the jacket 100.

FIG. 1B shows a plan view of the front side of the jacket 100, including the front cover 102, the case 104, and the transparent screen 108. Inside the jacket 100, a connector assembly 116 is provided which is configured to connect to an accessory port on the handheld device. In some embodiments, the connector assembly 116 can include a 30 pin connector suitable for use with an iPod Touch® and/or iPhone®. FIG. 1C shows a plan view of the back side of the jacket 100, including the back cover 118 and the protective case 104. The back side of the jacket 100 includes a transparent window 120, which can be aligned with a scan engine or scanner disposed inside the jacket 100. The scan engine can be a modular barcode scan engine such as a miniaturized, high performance 650 nm laser-based, single-line decoded scan engine from Symbol Technologies (model no. SE-923). The scan engine can be modular and self-contained, and can include a microcontroller configured to decode a barcode into a format compatible with and readable by the handheld device (or an application on the handheld device). In some embodiments, the scan engine is not configured to decode a barcode, and the terminal includes additional decoding or conversion circuitry configured to convert barcode data into an acceptable format for processing at slave microcontroller.

Figure 1D:
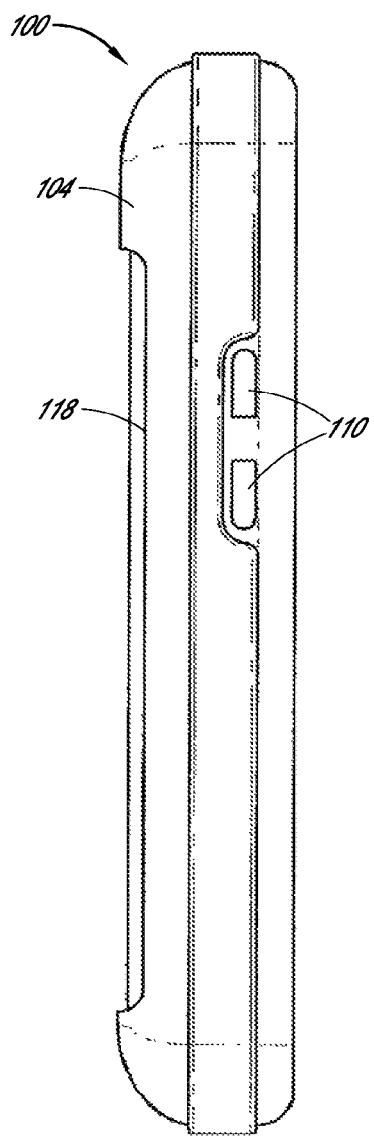
FIGS. 1D and 1E show left and right side views, respectively, of the jacket 100.
Figure 1E:
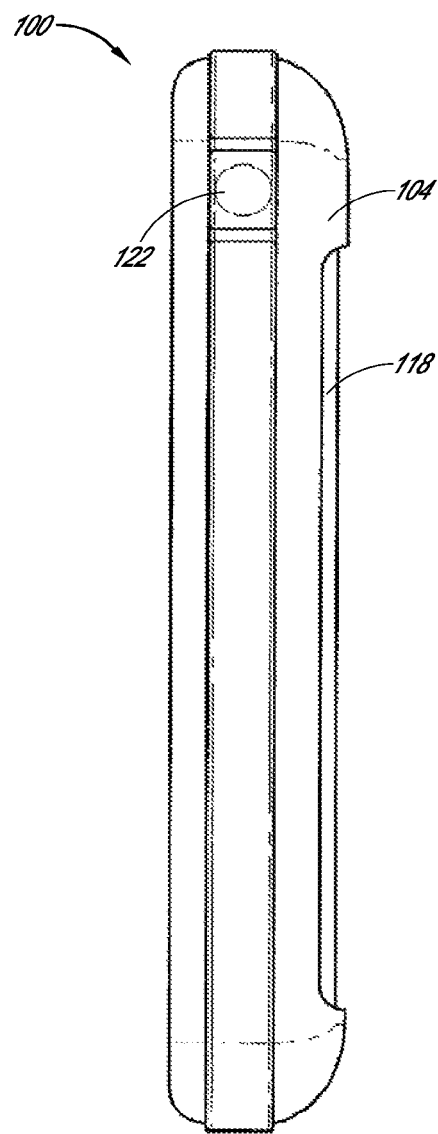

FIGS. 1D and 1E show left and right side views, respectively, of the jacket 100. As shown in FIG. 1E, the jacket 100 includes a scan button 122. The scan button 122 can be configured to activate the scan engine disposed inside the jacket 100. In some embodiments, the scan button 122 can be sized and shaped so that a user may hold the jacket 100 in one hand and manipulate the scan button with a thumb. In this way, the scan button 122 can be comfortably depressed or contacted by a user while viewing the screen 108 of the jacket 100. Although FIG. 1E illustrates the scan button 122 on the right side of the jacket 100, those having at least ordinary skill in the art will appreciate that the scan button 122 can be disposed on the left side of the jacket 100 so as to accommodate left handed users.

Figure 1F:
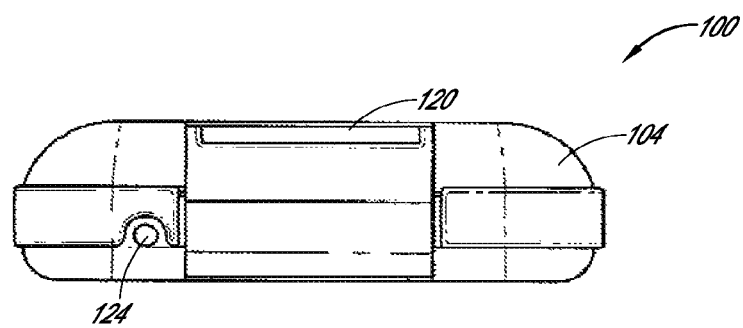
FIGS. 1F and 1G show top and bottom end views, respectively, of the jacket 100.
Figure 1G:
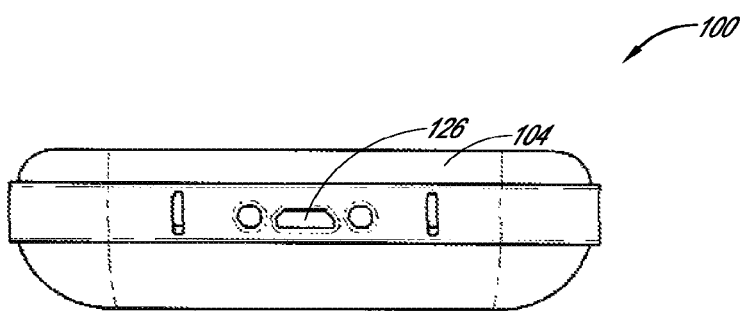

FIGS. 1F and 1G show top and bottom end views, respectively, of the jacket 100. As shown in FIG. 1F, the jacket 100 includes a pass-through button 124 which can be configured to align with an input button on the device and allow a user to access the input button on the device through the jacket 100. For example, the button 124 can be configured to align with a power button on the handheld device. As shown in FIG. 1G, the case 104 can include one or more openings, such as opening 126, configured to align with a connector on the connector assembly 116.

Figure 1H:
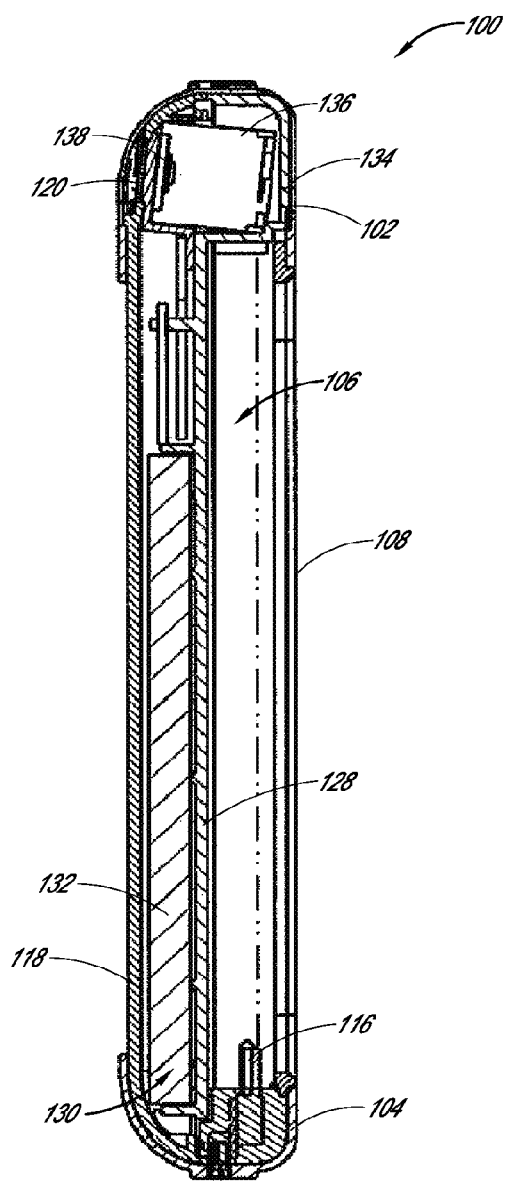
FIG. 1H shows a cross-section of the jacket 100 taken along line A-A of FIG. 1B.

FIG. 1H shows a cross-section of the jacket 100 taken along line A-A of FIG. 1B, and illustrates certain portions of the jacket 100 in further detail. For example, FIG. 1H shows an intermediate member 128 which can be disposed between the front cover 102 and the back cover 118. Together with the front cover 102 (and the transparent screen 108), the intermediate member 128 can define the receiving area 106 for the handheld device. Together with the back cover 118, the intermediate member 128 defines a receiving area 130 for a battery 132, as well as a receiving area 134 for a scan engine 136. The battery 132 can include a lithium polymer battery configured to supply power to the scan engine 136. As mentioned above, in some embodiments the battery 132 can supply power to a handheld device as well. In this way, the battery 132 can power the components of the jacket 100 and/or the handheld device for an extended period of time, for example, 12 hours or more.

In some applications, the jacket (or a component thereof) can include firmware that communicates with the battery 132 and controls basic operations of the jacket 100. The battery 132 can be an extended battery, for example allowing the scanning jacket 100 to be used by a caregiver for a full 12 hour shift. In some embodiments, when a handheld device is placed within the receiving area 106 and the connector assembly 116 is connected to a charging connector (or other accessory port) on the handheld device, the scan engine 136 can communicate with the handheld device or with an application on the handheld device, such as an inventory or patient-safety application or other process control application on the handheld device.

The scan engine 136 can include a scan window 138, which may be disposed so as to face in a generally normal direction with respect to the general plane of the jacket 100 (for example, the general plane of transparent screen 108 through which the device display may be viewed). By such a configuration, a user may view the device display while scanning an object, by holding the jacket 100 over the object. In some embodiments, as illustrated in FIG. 1H, the scan window 138 can be configured to face at a slight angle from the normal direction (for example, an angle of about 5°, 6°, 7°, 8°, 9°, 9.5°, 10°, 10.5°, 11°, 12°, 13°, 14°, or 15° from the normal direction, or an angle greater than, less than, or between any of these two listed angles; or an angle of about 70°, 71°, 72°, 73°, 74°, 75°, 76°, 77°, 78°, 79°, 79.5°, 80°, 80.5°, 81°, 82°, 83°, 84°, 85°, 86°, 87°, 88°, 89°, or 90° from a plane of the jacket 100, or an angle greater than, less than, or between any of these two listed angles). By such a configuration, a user may be able to see the object being scanned (such as, for example, an object being held in the user's other hand) just beyond the top of the device while the user is also viewing the device display. In this position, a user can also manipulate the scan button 122 with ease using a thumb. In other embodiments, the scan window 138 can be disposed so as to face a direction generally parallel to the plane of the jacket 100 (for example, straight ahead from the top end of the device), or at an angle to the top end of the device.

Figure 1I:
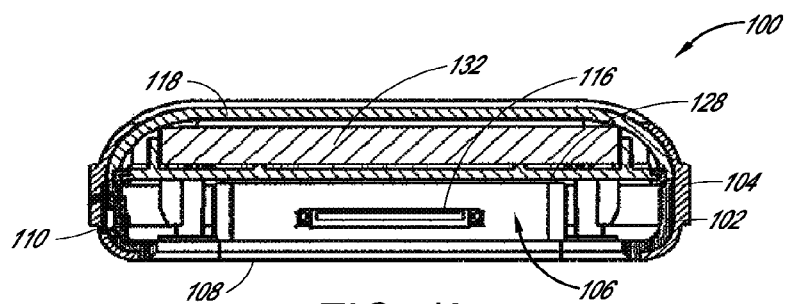
FIG. 1I shows a cross-section of the jacket 100 taken along line B-B of FIG. 1B.

In some embodiments, as illustrated in FIG. 1H, the scan window 138 can be recessed within the jacket, while in other embodiments, the scan window can protrude from a surface of the jacket. In some embodiments, the scan engine 136 (and/or the scan window 138) can be movable (for example, rotatable) so as to allow a user to select or alter the angle and/or orientation of the scan window 138. FIG. 1I shows a cross-section of the jacket 100 taken along line B-B of FIG. 1B, and further illustrates the receiving area 106, the connector assembly 116, and the configuration of the front cover 102, the back cover 118, and the intermediate member 128.

Figure 1J:
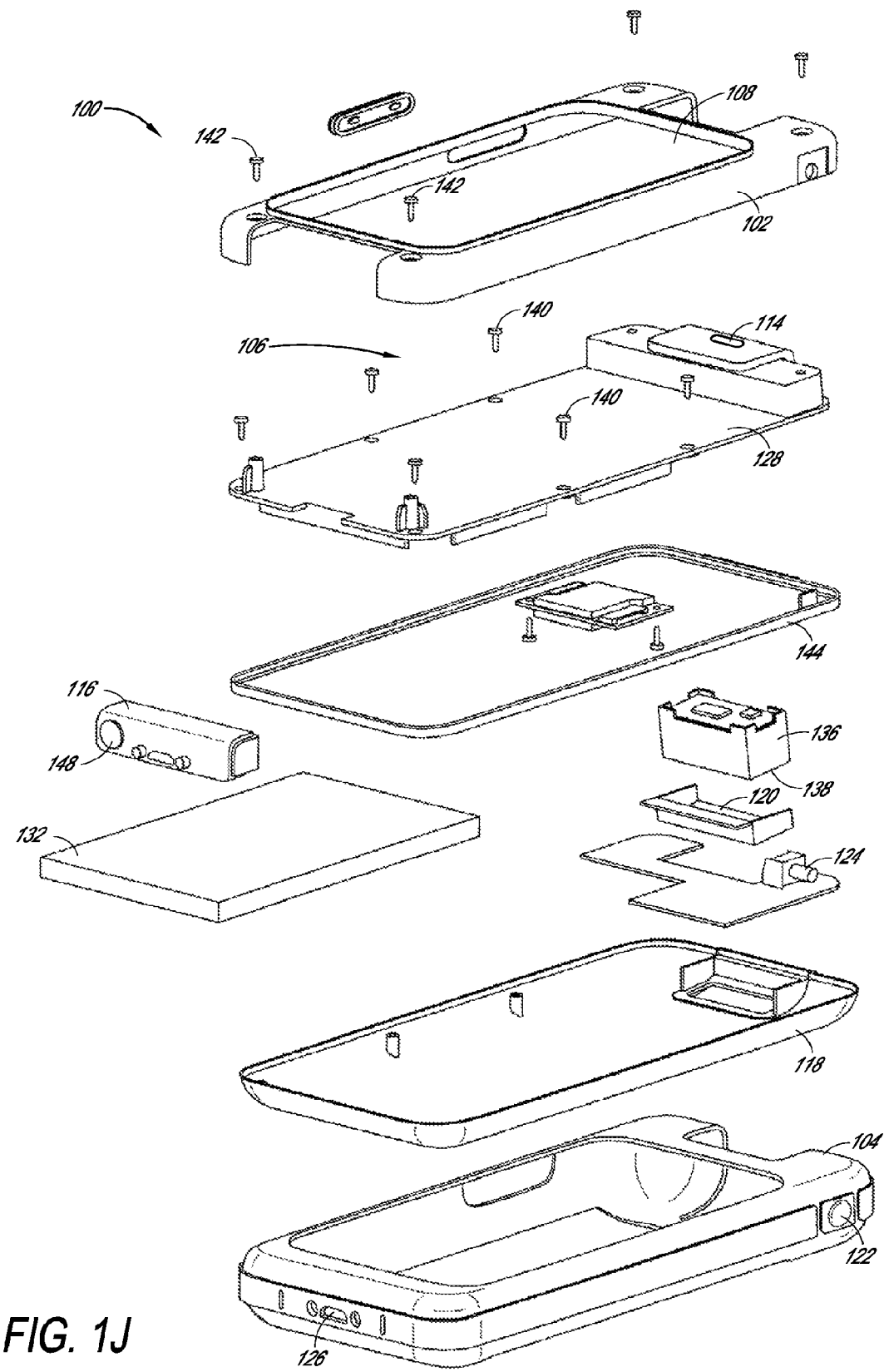
FIG. 1J shows an exploded view of the jacket 100 and its various components.

FIG. 1J shows an exploded view of the jacket 100 and its various components, including the front cover 102, the back cover 118, the intermediate member 128, the scan engine 136, and the transparent window 120. As can be seen in FIG. 1J, the jacket 100 can include a microphone 148, which may form part of the connector assembly 116. The microphone 148 and the speaker 114 can both be liquid-proof and/or liquid resistant, and can be configured to allow use of a non-cellular device as a VoIP handset in a healthcare setting.

As can also be seen in FIG. 1J, the intermediate member 128 and the back cover 118 can be fastened together using a plurality of fasteners, such as screws 140, so as to enclose the scan engine 136 and the battery 132 within the jacket 100. The front cover 102 can also be fastened together using a plurality of fasteners, such as screws 142, to enclose the receiving area 106 and the connector assembly 116. One or more gaskets 144 can be provided around the edges of the seams between the front cover 102, the intermediate member 128, and the back cover 118 and configured to provide a seal or boundary for the receiving area 106. In this way, the receiving area 106 can be sealed from liquids (water, blood, bodily fluids, medications, cleaning agents, etc.) and/or solid particles (medical powders, dust, dirt, debris, etc.) that the jacket 100 may be exposed to in use.

In some embodiments, the seal for the receiving area 106 can be configured to meet an ingress protection rating or international protection rating required or preferred for a particular use. For example, the jacket 100 can be configured to provide an "IP54" protection rating for the receiving area 106. As used herein, an IP54 protection rating refers to an enclosure that protects against the ingress of dust and other small particles in a quantity that would interfere with the satisfactory operation of the handheld device and that also protects the handheld device from liquid that splashes against the jacket 100 from any direction. Of course, the jacket 100 can be configured to provide more, or less, protection against the intrusion of solid particles and liquids into the receiving area 106 to protect the internal components (for example, the handheld device).

In some embodiments, the jacket 100 can include an actuator 146 disposed between the intermediate member 128 and the back cover 118, in alignment with the scan button 122 on the case 104, which is configured to activate the scan engine 136. Once the handheld device is in place in the receiving area 106 and connected to the connector assembly 116, with the front cover 102 and back cover 118 fastened together and the gasket 144 in place, the case 104 can be pulled around the covers 102, 118 to provide drop resistance as well as a comfortable grip. In some embodiments, the jacket 100 can have a shape that is comfortable to grip and that is also pleasing to the eye. The exterior of the jacket 100 (including, for example, portions of the front cover 102, the back cover 118, the case 104, and the areas joining these components) can be configured to resist liquid splashes and cleaning materials, allowing the jacket 100 to be regularly cleaned as per usual healthcare procedures for infection control. In other embodiments, the front and back covers 102, 118 can be covered or coated with a drop-resistant (for example, compressible) and liquid-proof or liquid resistant material, without the addition of a flexible case, and can be provided with an interengaging structure configured to create a seal to prevent the ingress of water and cleaning fluids. In this way, the front and back covers 102, 118 can provide another seal to protect internal components housed within the jacket 100.

Figure 2A:
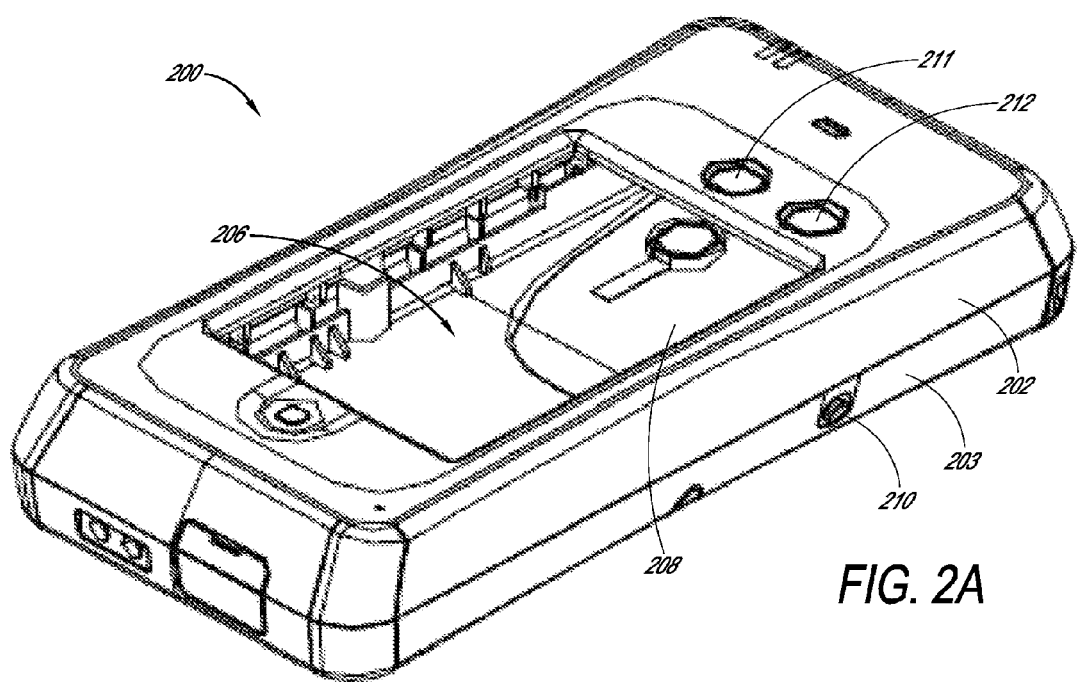
FIG. 2A shows a perspective view of a jacket 200 according to another embodiment.

FIG. 2A shows a perspective view of a jacket 200 according to another embodiment. The jacket 200 includes a front cover 202 and a back cover 203. The jacket 200 includes a receiving area 206 configured to receive a handheld device, such as an iPod Touch®. The front cover 202 includes a transparent screen 208 which is configured to align with a display on the handheld device. The transparent screen 208 can also be configured to allow a user to interact with a touchscreen or other input mechanism on the handheld device. Either or both of the front cover 202 and back cover 203 can include a scan button 210 which is configured to activate a scan engine disposed inside the jacket 200. The front cover 202 (and/or the back cover 203) can also include windows 211, 212 configured to align with and allow operation of a light sensor and camera, respectively, on the handheld device.

Figure 2D:
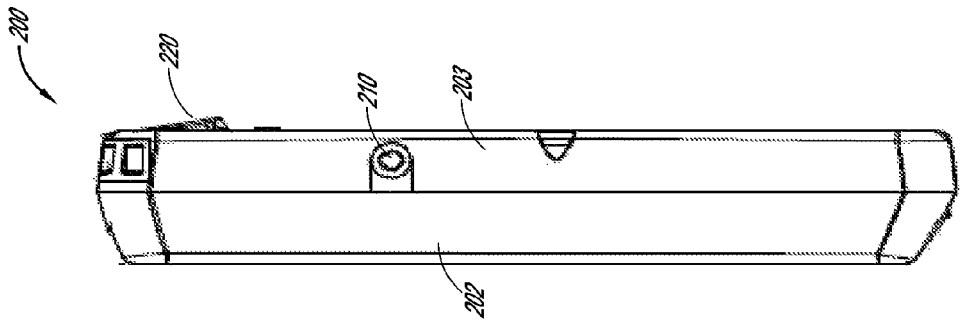
FIG. 2D shows a right side view of the jacket 200.
Figure 2B:
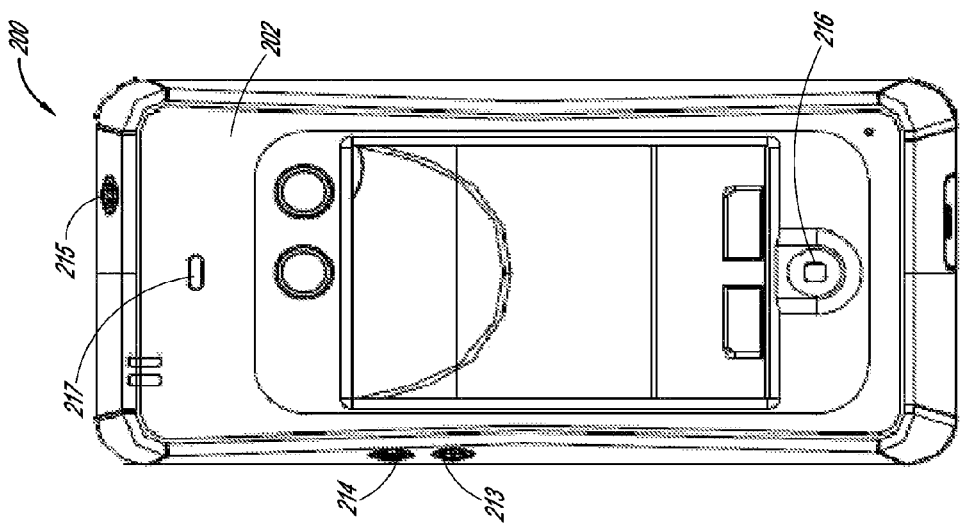
FIG. 2B shows a plan view of the front side of the jacket 200.

FIG. 2B shows a plan view of the front side of the jacket 200. As shown in FIG. 2B, the front cover 202 (and/or the back cover 203) can include one or more pass-through buttons, such as pass-through buttons 213, 214, 215, and 216, which are configured to align with input buttons on the device and allow a user to access the input buttons on the device through the jacket 200. In the illustrated embodiment, the buttons 213, 214 are configured to align with volume control buttons on the handheld device and the button 215 is configured to align with a power button on the handheld device. The button 216 is configured to align with a menu button on the handheld device. The jacket 200 can also include an earpiece 217.

Figure 2C:
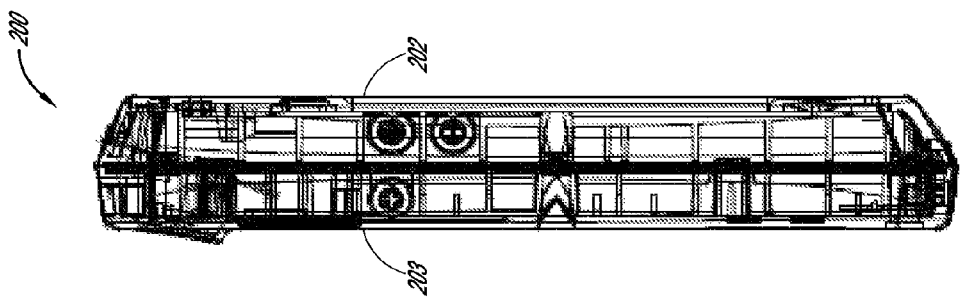
FIG. 2C shows a cross-sectional view of the jacket 200.
Figure 2F:
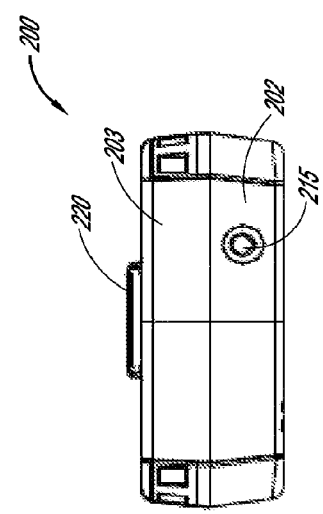
FIGS. 2F and 2G show top and bottom end views, respectively, of the jacket 200.
Figure 2G:
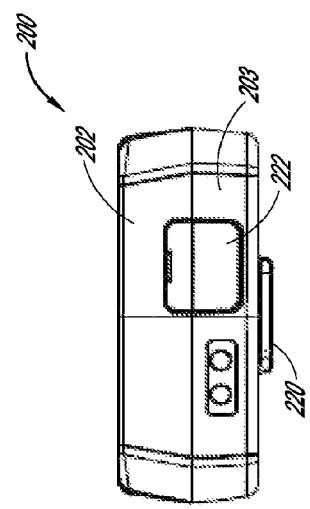
Figure 2E:
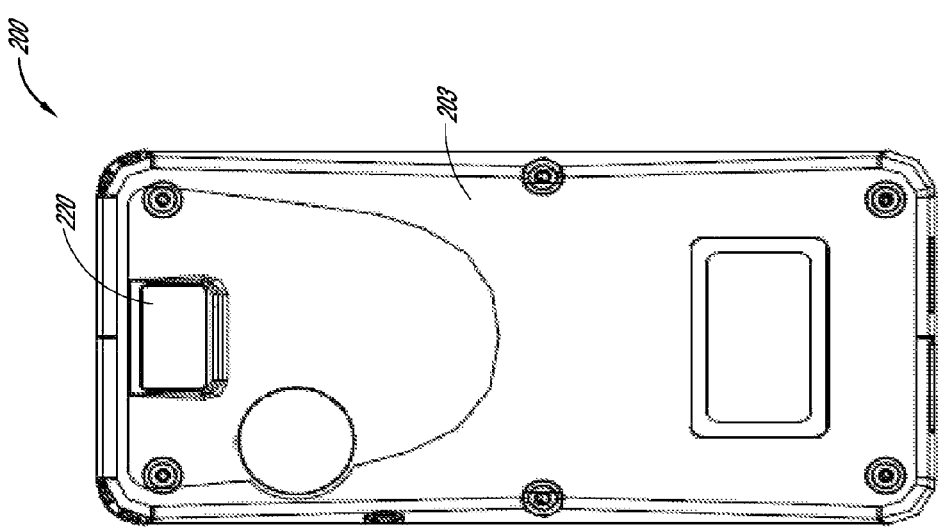
FIG. 2E shows a plan view of the back side of the jacket 200.

FIG. 2C shows a cross-sectional view of the jacket 200, and FIG. 2D shows a right side view of the jacket 200. FIG. 2D illustrates a scan window 220 protruding from the back cover 203 at an angle with respect to the plane of the jacket 200. The scan window 220 can be aligned with, or form part of, a scan engine or scanner disposed inside the jacket 100. The scan engine can be a modular barcode scan engine such as a miniaturized, high performance 650 nm laser-based, single-line decoded scan engine from Symbol Technologies (model no. SE-923). The scan engine can be modular and self-contained, and can include a microcontroller configured to decode a barcode into a format compatible with and readable by the handheld device (or an application on the handheld device). FIG. 12E shows a plan view of the back side of the jacket 200, including the scan window 220. FIGS. 12F and 12G show top and bottom end views, respectively, of the jacket 200. FIG. 12G illustrates a charging slot 222 which can be used to provide electrical access to a handheld device disposed within the jacket 200.

Figure 3A:
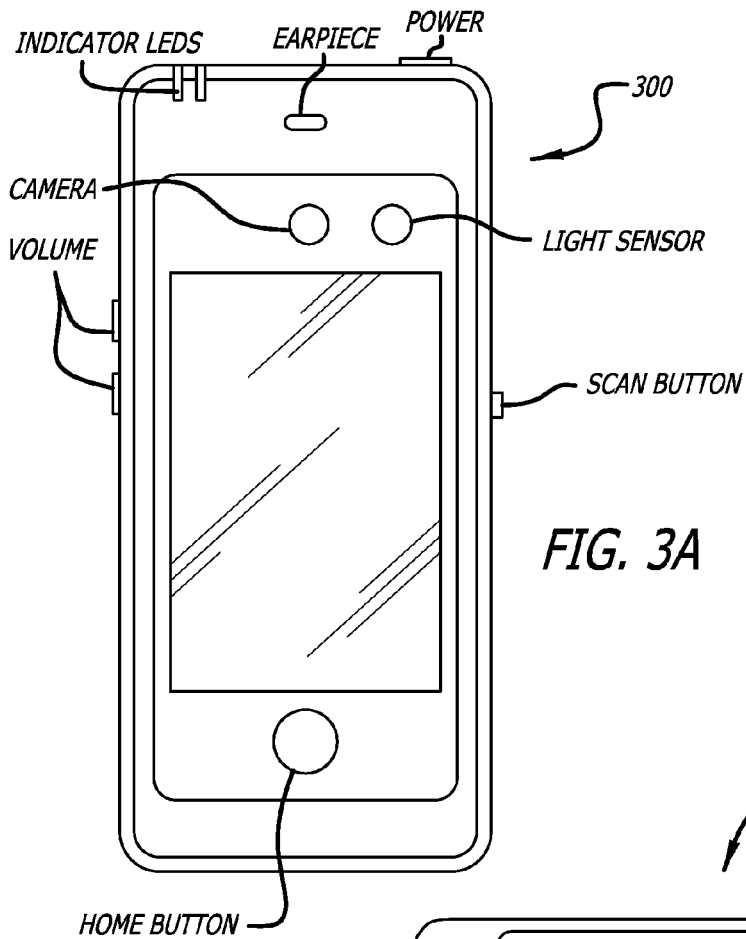
FIG. 3A is a drawing showing the front of a jacket 300 according to another embodiment.
Figure 3B:
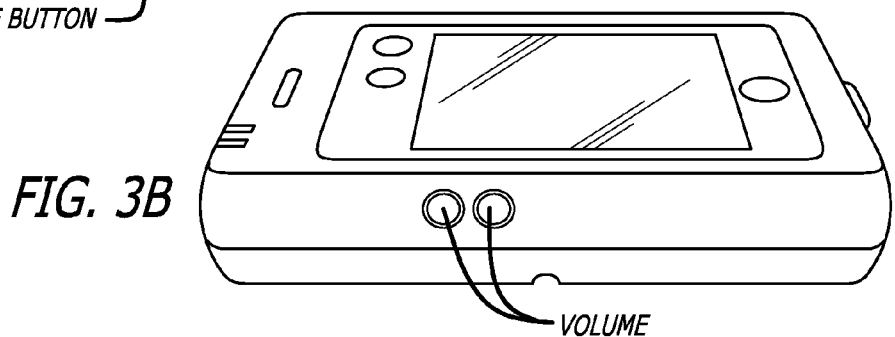
FIG. 3B is a drawing showing the left side of the jacket 300.
Figure 3C:
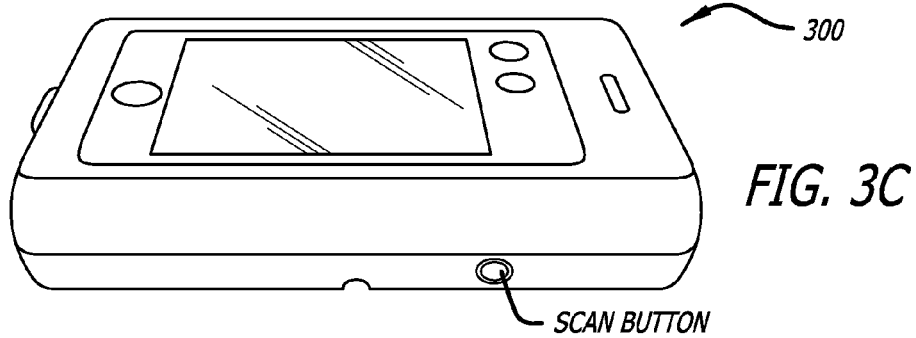
FIG. 3C is a drawing showing the right side of the jacket 300.
Figure 3D:
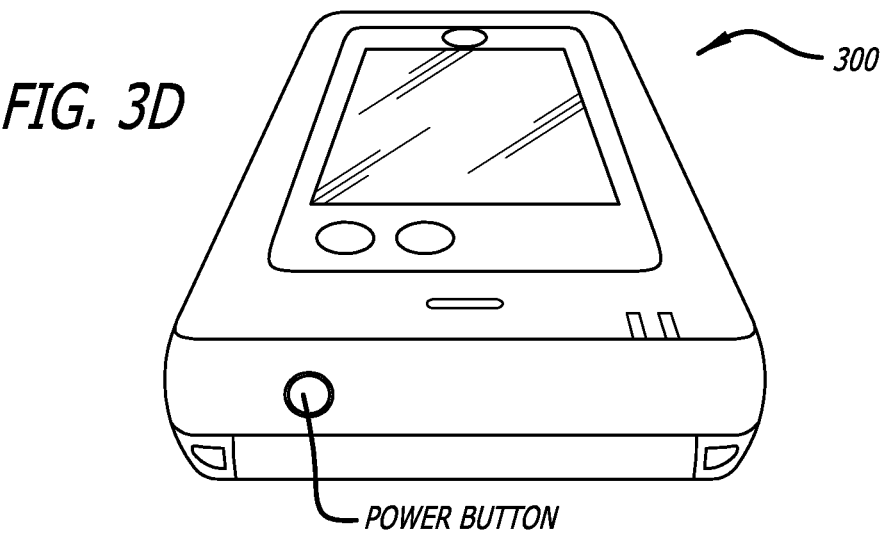
FIG. 3D is a drawing showing the top end of the jacket 300.
Figure 3E:
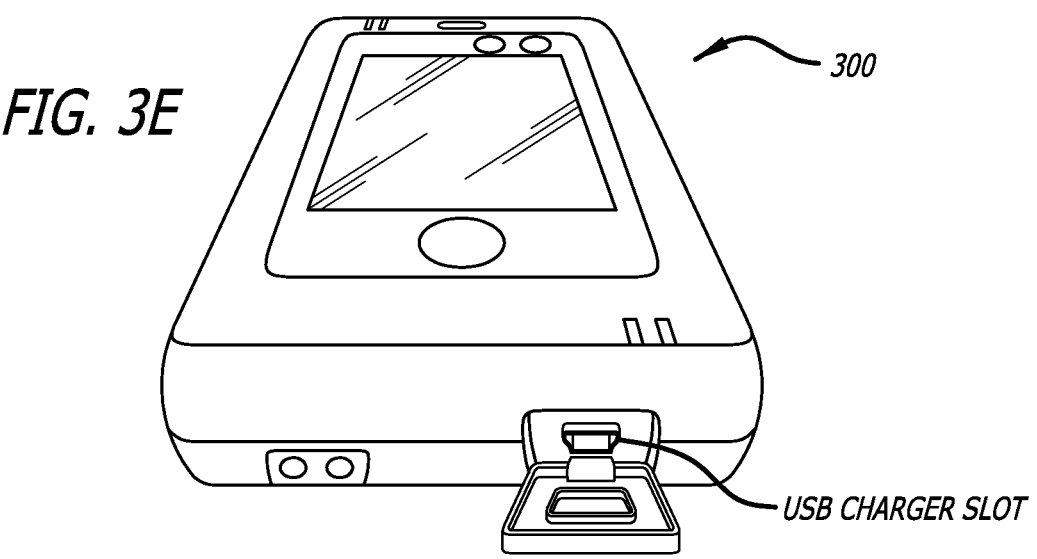
FIG. 3E is a drawing showing the bottom end of the jacket 300.
Figure 3G:
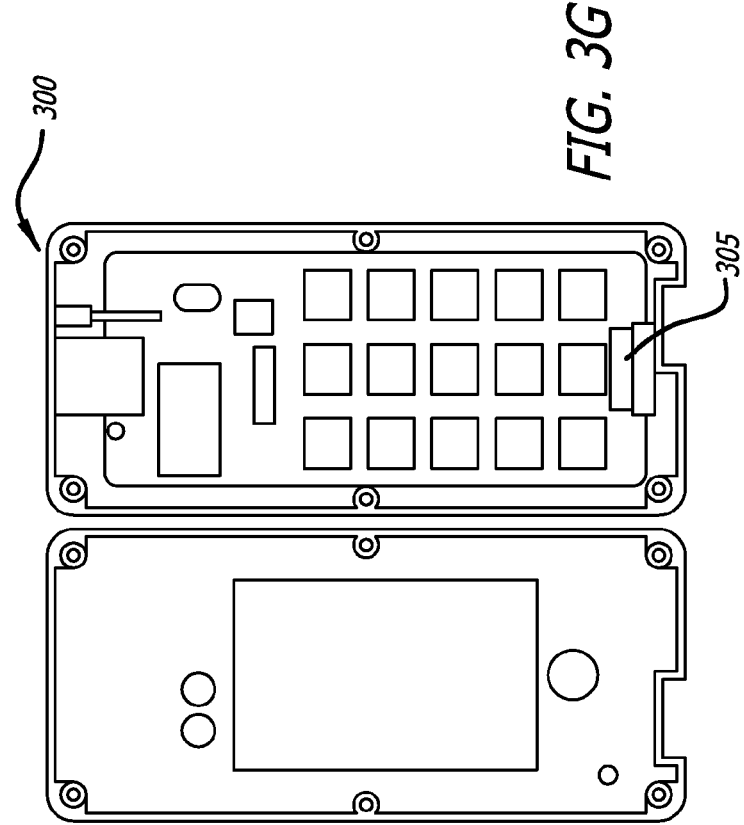
FIG. 3G is a drawing showing the jacket 300 in an open position.
Figure 4:
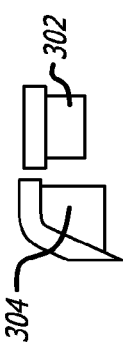
FIG. 4 is a drawing showing plugs that can be used with the jacket 300.
Figure 3F:
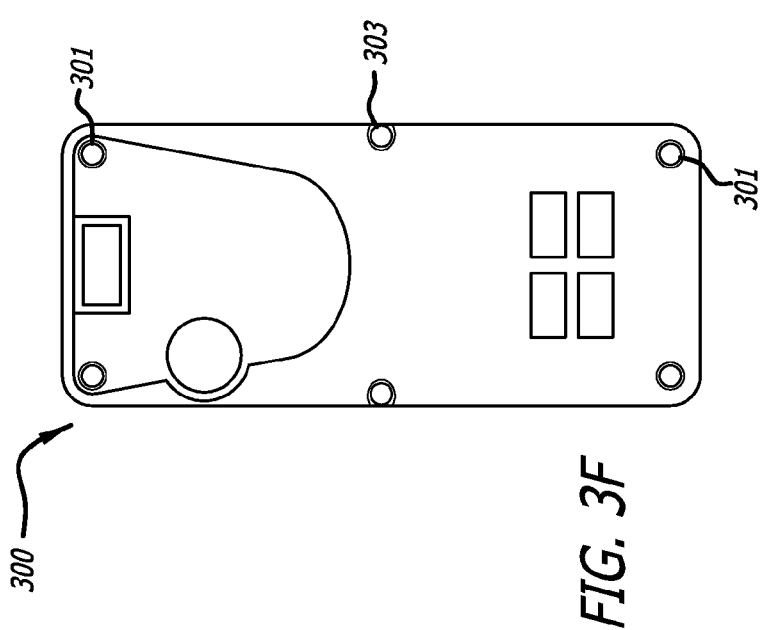
FIG. 3F is a drawing showing the back side of the jacket 300.

FIG. 3A is a drawing showing the front of a jacket 300 according to another embodiment. FIG. 3B is a drawing showing the left side of the jacket 300. FIG. 3C is a drawing showing the right side of the jacket 300. FIG. 3D is a drawing showing the top end of the jacket 300. FIG. 3E is a drawing showing the bottom end of the jacket 300. FIG. 3F is a drawing showing the back side of the jacket 300, including screw holes 301, 303. FIG. 3G is a drawing showing the jacket 300 in an open position, with a connector assembly 305 exposed, ready to receive a handheld device. FIG. 4 is a drawing showing plugs 302, 304 that can be used to seal screw holes or openings 301, 303, respectively, in the jacket 300.

Figure 5A:
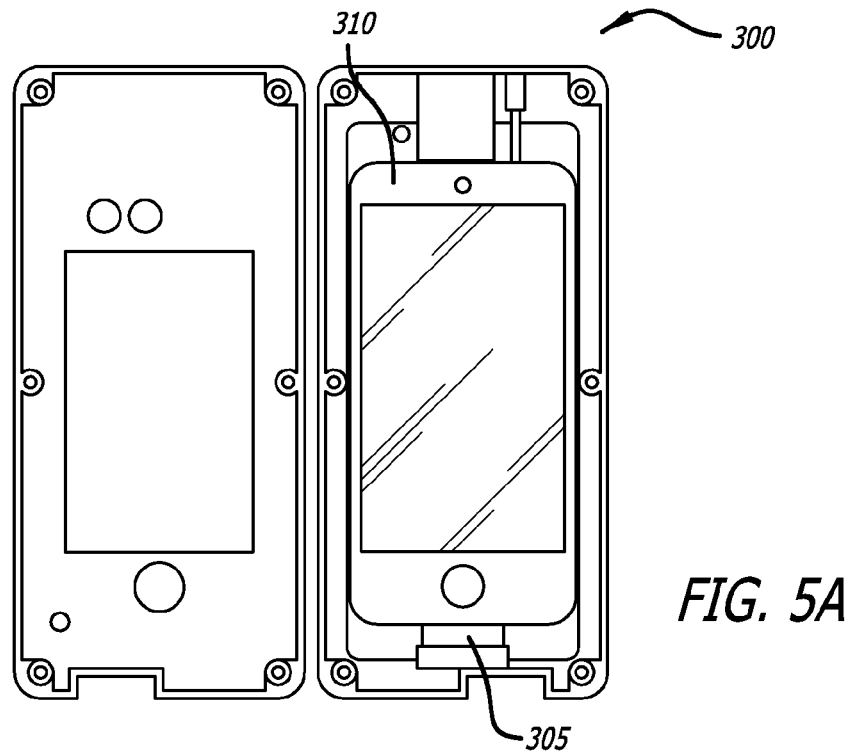
FIGS. 5A and 5B are drawings illustrating steps in the installation of a handheld electronic device in the jacket 300.
Figure 5B:
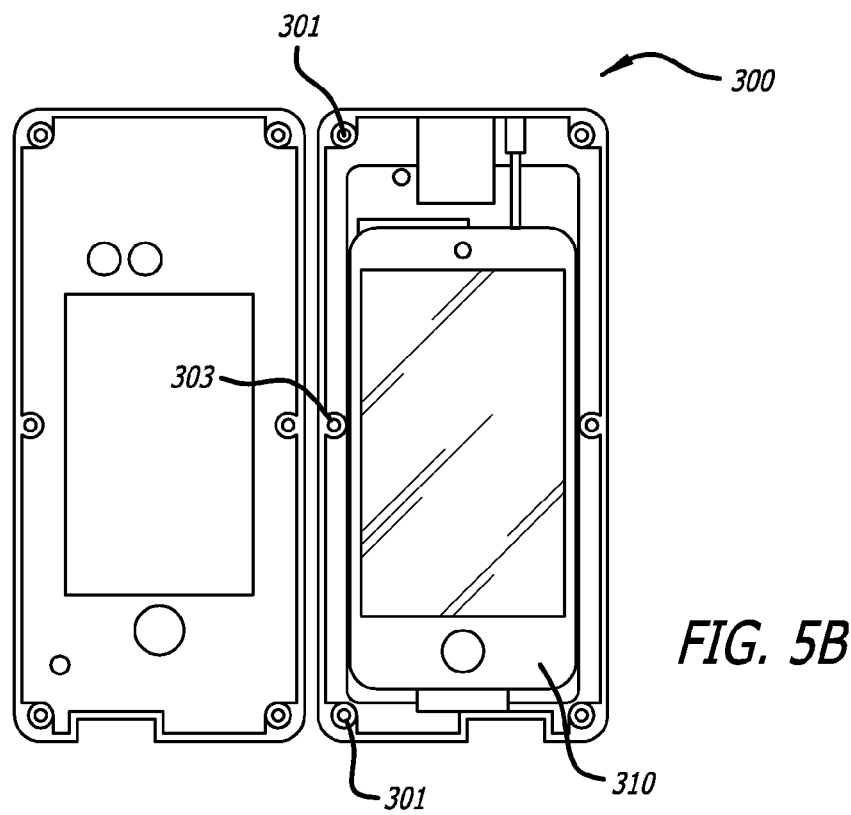

FIGS. 5A and 5B are drawings illustrating steps in the installation of a handheld electronic device 310 in the jacket 300. For example, with the jacket 300 in an open position (FIG. 5A), the handheld device 301 can be placed into the jacket 300 at a slight upward-facing angle. The connector assembly 305 is braced at the bottom (as indicated in FIG. 5B) and the device 310 is slid down fully to make a solid connection with the connector assembly 305. The front cover is then placed over the handheld device 310, in alignment with the back cover. After fasteners are installed in the corner screw holes 301 and the side screw holes 303, the plugs 302, 304 can be inserted into the corner screw holes 301 and the side screw holes 303, respectively, to seal the holes 301, 303.

As with the embodiments of jackets described above, the jacket 300 can include sealing or engaging structure to seal internal components, including the handheld device 301 and other electronic components, within the jacket 300. The jacket 300 can further include one or more batteries, an optical scanner, and/or a scanner engine. In this way, the jacket 300 and handheld device 301 can form a handheld terminal or computing device that may be used comfortably by a healthcare professional over the course of a work shift to perform one or more tasks. For example, a handheld terminal including the jacket 300 and handheld device 301 can be used to scan codes in a hospital environment without requiring power charges and with minimal risk of damage to the terminal from exposure to solid particles and/or liquids. Further, the jacket 300 can include one or more materials that can be repeatedly cleaned or disinfected using liquid agents without degrading over time.

Figure 6A:
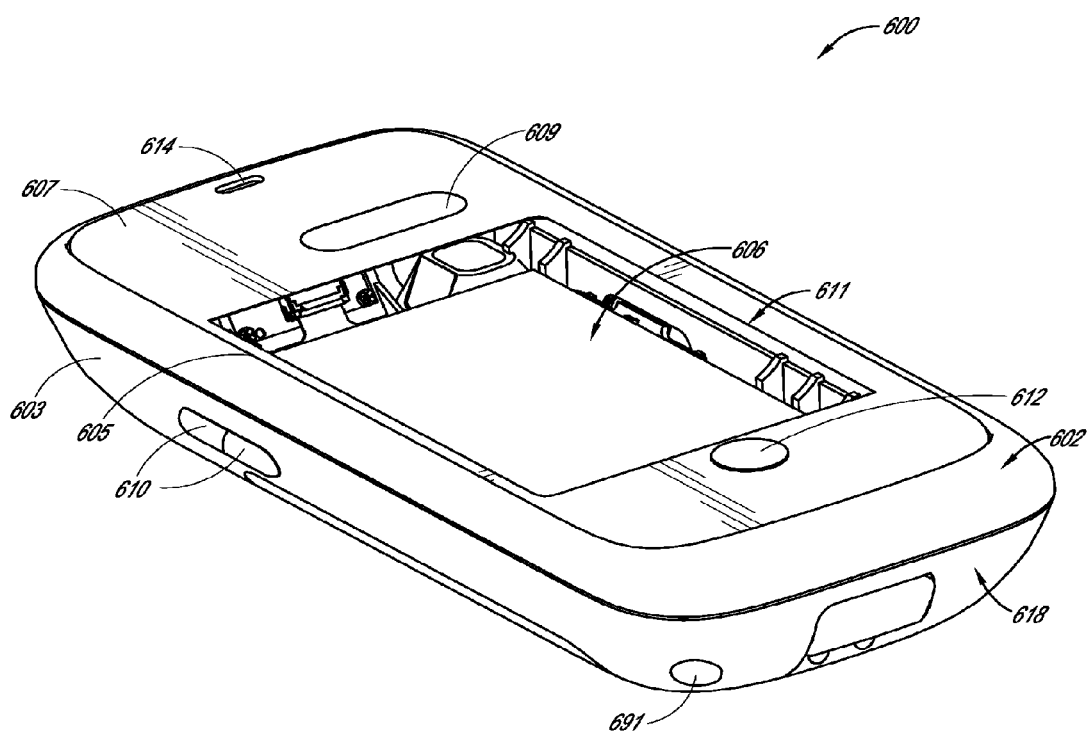
FIG. 6A shows a perspective view of a jacket 600 according to an embodiment.

FIG. 6A shows a perspective view of a jacket 600 according to another embodiment. As with the jackets described above, the jacket 600 can be used to form a handheld terminal or computing device along with a handheld device (not shown). For example, the jacket 600 can be configured to at least partially house and/or encase a handheld device, for example, an iPod Touch®, such that the handheld device can be utilized to perform one or more tasks, such as tasks performed in a healthcare environment.

In some embodiments, the jacket 600 is designed to fit ergonomically and/or comfortably in a single hand of a user. As shown, to facilitate an ergonomic and/or comfortable grip, the jacket 600 can include rounded outer contours, edges, and/or surfaces such that a user's hand is not exposed to features. Further, the jacket 600 can be formed of a resilient material, for example, a polycarbonate material. In addition to providing the function of an ergonomic and/or comfortable grip, the jacket 600 can be configured to be aesthetically pleasing to the eye, in some embodiments.

Still referring to FIG. 6A, the jacket 600 can include an upper or front cover 602 and a lower or back cover 618. The front and back covers 602, 618 can form the outer surfaces of the jacket 600 that may be contacted by a user. Further, the jacket 600 includes a receiving area 606 configured to receive a handheld device, such as an iPod Touch®.

A receiving area 606 can be disposed between the front and back covers 602, 618 and can be accessible through an opening 611 formed in the front cover 602. In some embodiments, the opening 611 can be sized and shaped so as to align with at least a portion of a screen, display surface, and/or input surface of a handheld device. In this way, a screen of a handheld device received within the receiving area 606 may be directly contacted via the opening 611. As a result, the sensitivity of pressure-based, capacitance-based, and/or optical-based touch input systems can be preserved via direct user contact through the opening 611 when a handheld device is disposed within the receiving area 606 between the front and back covers 602, 618.

As shown, the front cover 602 can include an outer portion 603 which meets an inner portion 607 at a leading edge 605. The outer and inner portions 603, 607 can be sloped such that the leading edge 605 is offset or disposed above the plane of the opening 611. In this way, the exposed screen of a handheld device disposed within the receiving area 606 can be offset or set back from the leading edge 605. Accordingly, the leading edge 605 may protect the screen from damage when the front cover 602 of the jacket 600 comes into contact with another object, for example, when accidentally dropped, by forming a leading point of contact with the other object. Further, the back cover 618 can include one or more resilient protrusions 691 extending outwardly from the center of the jacket 600. Such protrusions 691 can be sized and/or shaped to at least partially absorb impactful forces that the jacket 600 may be exposed to. For example, the protrusions 691 can be sized and/or shaped to absorb impact forces when one or more of the protrusions contact a ground surface during a fall. Additionally, the protrusions 691 can increase frictional forces between the jacket 600 and another object, for example, a clip board, desk, or counter, to inhibit unintended movement of the jacket 600 due to incidental forces.

The front cover 602 and the back cover 618 can include one or more pass-through buttons, such as pass-through buttons 610 and 612, configured to align with input buttons on the device and allow a user to access the input buttons on the device through the jacket 600. In the illustrated embodiment, the buttons 610 are configured to align with volume control buttons on the handheld device and the button 612 is configured to align with a menu button on the handheld device. The jacket 600 can also include a speaker 614 which can be connected with an audio out terminal of a handheld device, for example. In some embodiments, the front cover 602 can include a transparent window 609 to allow for a forward facing camera of handheld device to be optically exposed through the transparent window when the handheld device is disposed within the receiving area 606 of the jacket 600.

Figure 6B:
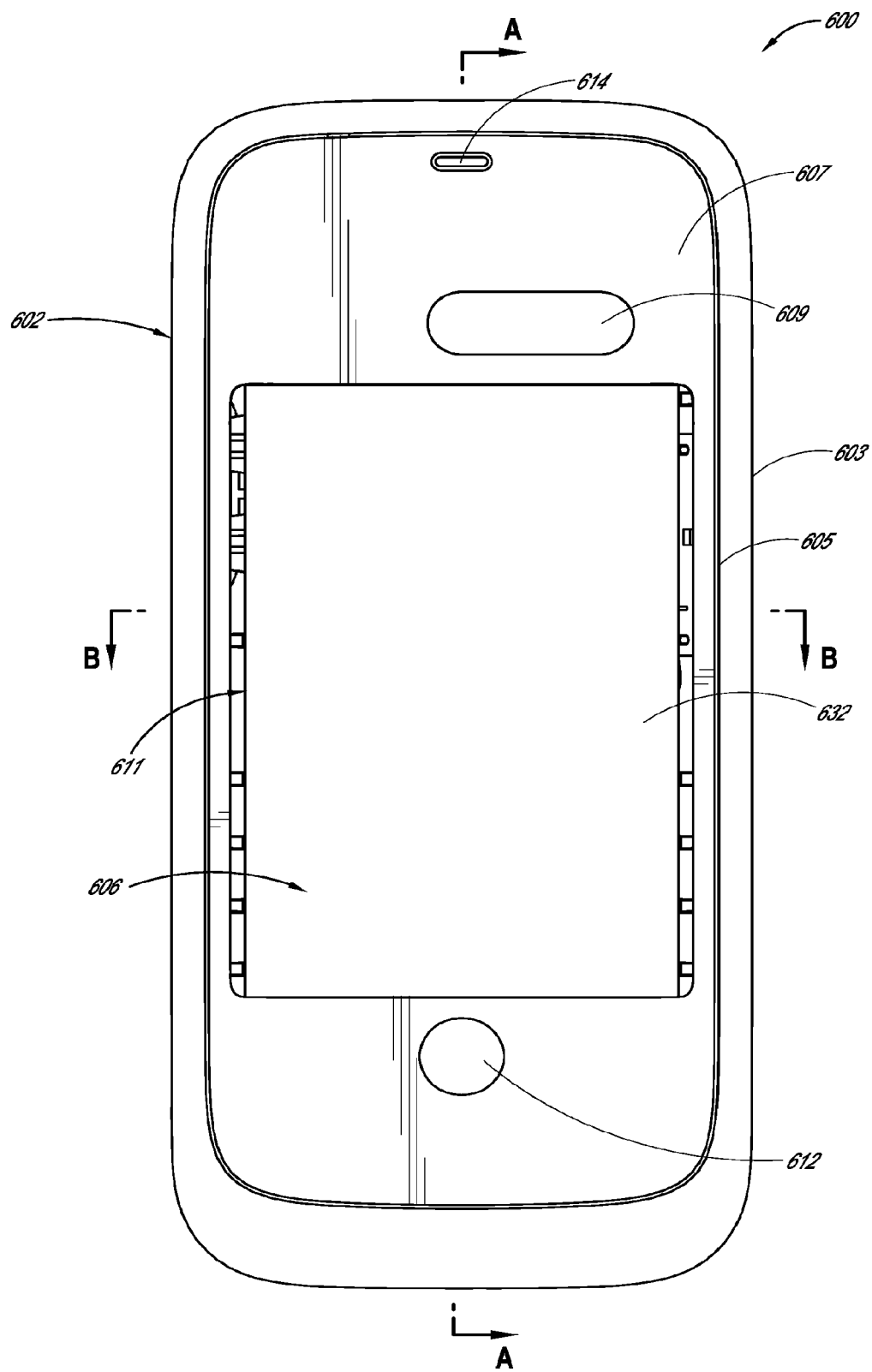
FIG. 6B shows a plan view of the front side of the jacket 600.

FIG. 6B shows a plan view of the front side of the jacket 600, including the front cover 602, the opening 611, and the receiving area 606. As shown, a battery 632 can be disposed within the jacket 600. In some embodiments, the battery 632 can provide a supporting surface to support a received handheld device above other components of the jacket 600 within the receiving area 606.

Figure 6C:
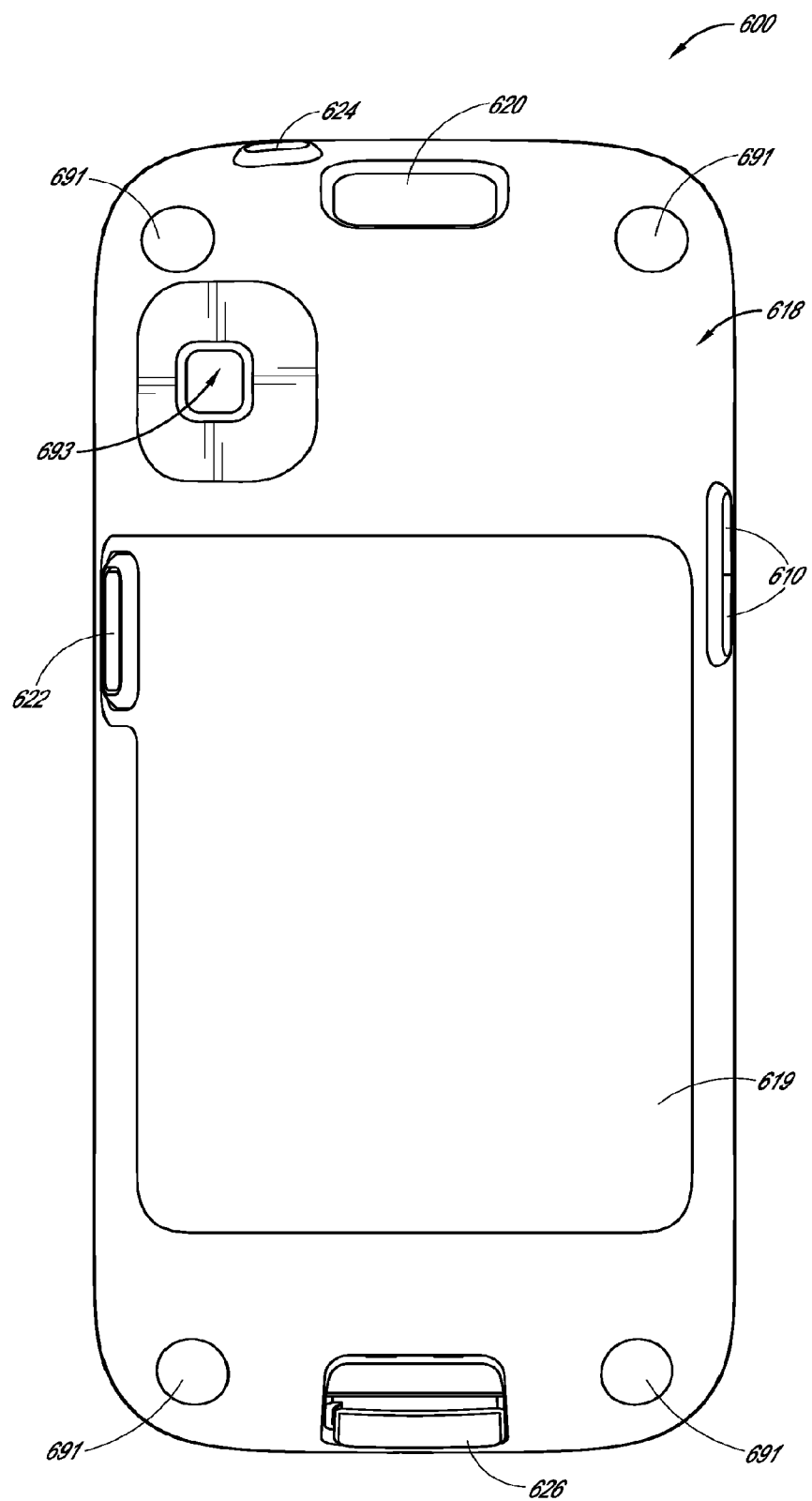
FIG. 6C shows a plan view of the back side of the jacket 600.

FIG. 6C shows a plan view of the back side of the jacket 600, including the back cover 618. In some embodiments, the back cover 618 can include a contact portion 619. The contact portion 619 can be sized and shaped to contact the inner portion of a user's hand that holds the back cover 618 of the jacket 600. In some embodiments, the contact portion 619 includes a scan button 622 disposed on a side of the jacket 600. In this way, in use, the inside of a user's hand can be disposed in contact with the contact portion 619 and the user's thumb may comfortably contact the scan button 622. In some embodiments, the contact portion 619 comprises a different material than other portions of the back cover 618. For example, the contact portion 619 can comprise a softer or less rigid structure that is comfortable to hold for extended periods of time. Further, the contact portion 619 can include an at least partially absorbent material to absorb oils and/or sweat from a user's hand.

Still referring to FIG. 6C, the back cover 618 of the jacket 600 can include a transparent scanning window 620, which can be aligned with a scan engine or scanner disposed within the jacket 600. The scan engine can be a modular barcode scan engine such as a miniaturized, high performance barcode scanning imager from Intermec (for example, model EA15). The scan engine can be modular and self-contained, and can include a microcontroller configured to decode a barcode into a format compatible with and readable by the handheld device (or an application on the handheld device). In some embodiments, the scan engine is not configured to decode a barcode, and the terminal further comprises additional decoding or conversion circuitry configured to convert barcode data into an acceptable format for processing at the slave microcontroller.

In some embodiments, the back cover 618 of the jacket 600 can optionally include another transparent window 693. The transparent window 693 can be aligned with a camera of a handheld device received within the jacket 600. Thus, the jacket 600 can form a handheld terminal including a handheld device which allows for scanning objects through the scanning window 620 and/or capturing images through the transparent window 693 via the handheld device. In some embodiments, the jacket 600 can include one or more lenses aligned with the transparent window 693 to alter the optical properties through the window 693. The back cover 618 also may include an opening 626, which will be described below with reference to FIG. 6G.

Figure 6D:
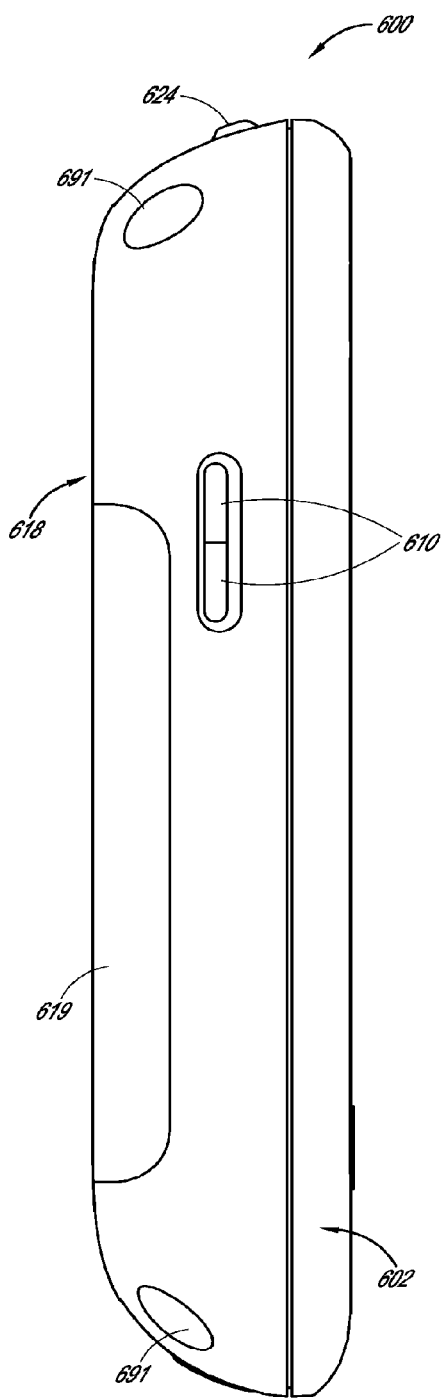
FIGS. 6D and 6E show left and right side views, respectively, of the jacket 600.
Figure 6E:
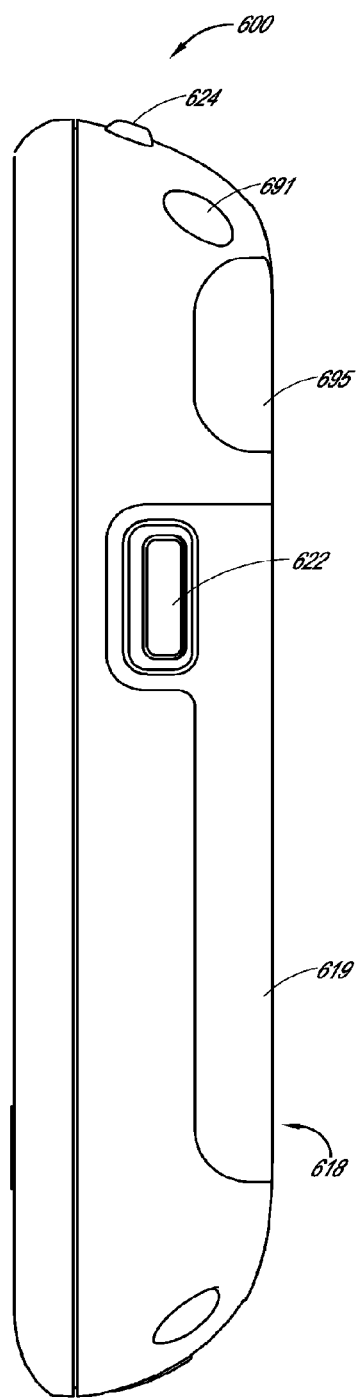

FIGS. 6D and 6E show left and right side views, respectively, of the jacket 600. As shown in FIG. 6E, the scan button 622 can be disposed on the right side of the jacket 600. The scan button 622 can be configured to activate the scan engine disposed inside the jacket 600. As discussed above, in some embodiments, the scan button 622 can be sized and shaped so that a user may hold the jacket 600 in one hand and manipulate the scan button with a thumb. In this way, the scan button 622 can be comfortably depressed or contacted by a user while viewing the screen of a handheld device through the opening 611 of the jacket 600. Although FIG. 6E illustrates the scan button 622 on the right side of the jacket 600, those having at least ordinary skill in the art will appreciate that the scan button 622 can be disposed on the left side of the jacket 600 so as to accommodate left handed user's, in some embodiments.

Figure 6F:
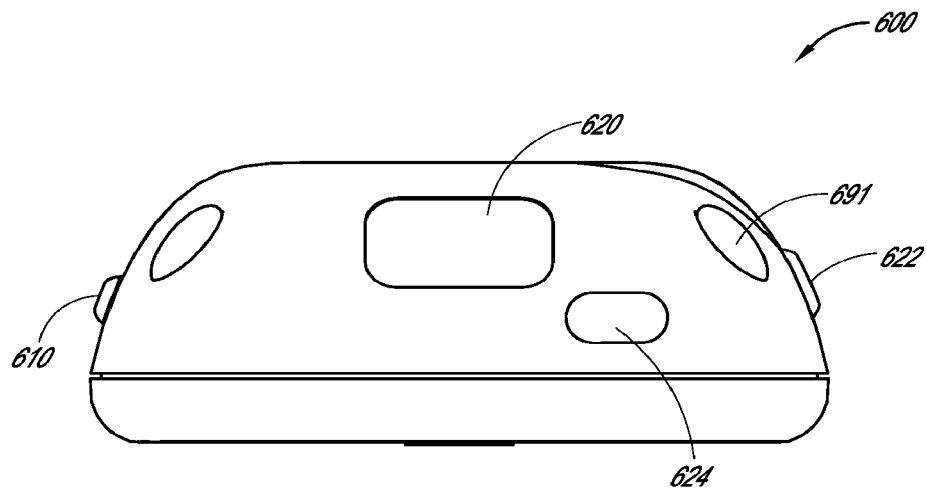
FIGS. 6F and 6G show top and bottom end views, respectively, of the jacket 600.
Figure 6G:
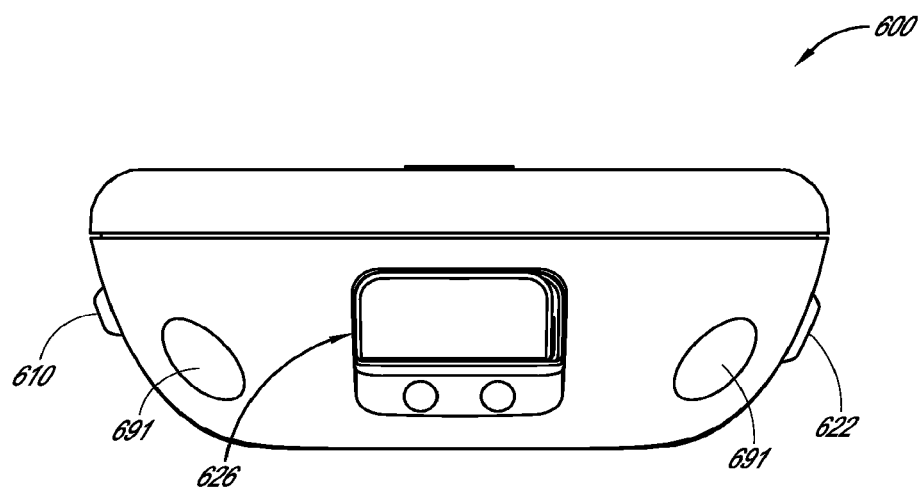

FIGS. 6F and 6G show top and bottom end views, respectively, of the jacket 600. As shown in FIG. 6F, the jacket 600 includes a pass-through button 624 which can be configured to align with an input button on the device and allow a user to access the input button on the device through the jacket 600. For example, the button 624 can be configured to align with a power button and/or hard reset on the handheld device. As shown in FIG. 6G, the jacket 600 can include one or more openings, such as opening 626, configured to align with a connector of a connector assembly disposed within the jacket 600.

Figure 6H:
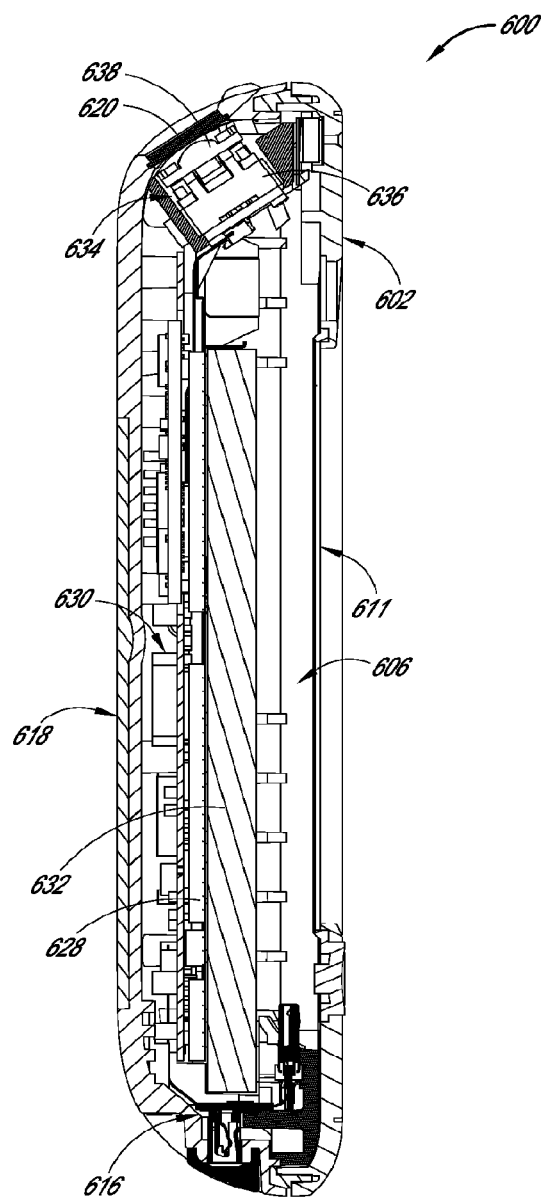
FIG. 6H shows a cross-section of the jacket 600 taken along line A-A of FIG. 6B.

FIG. 6H shows a cross-section of the jacket 600 taken along line A-A of FIG. 6B, and illustrates certain portions of the jacket 600 in further detail. For example, FIG. 6H shows a shield 628 which can be disposed underneath the battery 632 to shield underlying electrical components, for example, a scanner board and/or main circuit board. The battery 632 can include a lithium polymer battery configured to supply power to a scan engine 636. As mentioned above, in some embodiments the battery 632 can supply power to a handheld device as well. In this way, the battery 632 can power the components of the jacket 600 and/or the handheld device for an extended period of time, for example, 12 hours or more.

Still referring to FIG. 6H, the front cover 602 and battery 632 can form the receiving area 606 for the handheld device. Together with the back cover 618, the shield 628 defines a receiving area 630 for other components including a scanner board and/or main circuit board. In some applications, the jacket 600 (or a component thereof) can include firmware stored on memory of a main circuit board that communicates with the battery 632 and controls basic operations of the jacket 600.

In some embodiments, the scan engine 636 can include a scan window 638, which may be disposed so as to face in a generally normal direction with respect to the general plane of the jacket 600 (for example, the general plane of the opening 611 defined by the front cover 602). As shown, the scan window 638 can be at least partially aligned with the transparent scanning window 620 such that an optical path may be created between an object to be scanned and the scan engine 636 through the transparent scanning window 620 and the scan window 638. By such a configuration, a user may view the screen of the device while scanning an object, by holding the jacket 600 over the object and orienting the transparent scanning window 620 relative to the object to be scanned. In some embodiments, the scan window 638 may include one or more lenses, to alter the optical properties through the scan window 638.

In some embodiments, the scan window 638 can be configured to face at a slight angle from the normal direction (for example, an angle of about 5°, 6°, 7°, 8°, 9°, 9°, 10°, 10.5°, 11°, 12°, 13°, 14°, or 15° from the normal direction, or an angle greater than, less than, or between any of these two listed angles; or an angle of about 70°, 71°, 72°, 73°, 74°, 75°, 76°, 77°, 78°, 79°, 79.5°, 80°, 80.5°, 81°, 82°, 83°, 84°, 85°, 86°, 87°, 88°, 89°, or 90° from a plane of the jacket 600, or an angle greater than, less than, or between any of these two listed angles). By such a configuration, a user may be able to see the object being scanned (such as, for example, an object being held in the user's other hand) just beyond the top of the device while the user is also viewing the device display. In this position, a user can also manipulate the scan button 622 with ease using a thumb. Thus, the user does not have to torque or twist the wrist to move between a position where an object is viewable but not scannable to another position where the object is scannable but not viewable.

In other embodiments, the scan window 638 can be disposed so as to face a direction generally parallel to the plane of the jacket 600 (for example, straight ahead from the top end of the device), or at an angle to the top end of the device. In some embodiments, as illustrated in FIG. 6H, the scan window 638 can be recessed within the jacket 600, while in other embodiments, the scan window can protrude from a surface of the jacket. In some embodiments, the scan engine 636 (and/or the scan window 638) can be movable (for example, rotatable) so as to allow a user to select or alter the angle and/or orientation of the scan window 638. FIG. 6H also includes a connector assembly 616, which will be described below with regard to FIG. 6I.

Figure 6I:
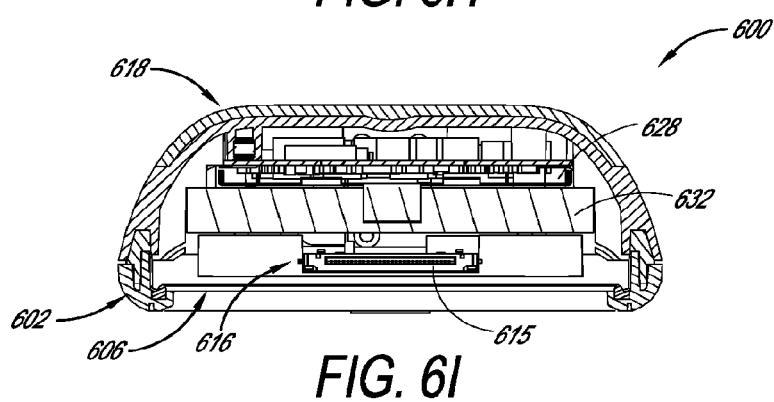
FIG. 6I shows a cross-section of the jacket 600 taken along line B-B of FIG. 6B.

FIG. 6I shows a cross-section of the jacket 600 taken along line B-B of FIG. 6B, and further illustrates the receiving area 606, and a connector assembly 616. Inside the jacket 600, the connector assembly 616 is provided which is configured to connect to an accessory port on the handheld device. In some embodiments, the connector assembly 616 can include a 30 pin connector 615 suitable for use with an iPod Touch® and/or iPhone®. The connector assembly 616 may be accessible through the opening 626 shown in FIG. 6G such that a handheld device disposed within the receiving area 606 may be connected to via the opening 626, the connector assembly 616 and the connector 615. In some embodiments, the connector assembly 616 can include a female usb port configured to convert a usb connection to a 30 pin connector through the connector assembly 616. In this way, a user may connect to the handheld device with a connection structure that is different than a pin configuration of the connection port of the handheld device. In some embodiments, when a handheld device is placed within the receiving area 606 and the connector assembly 616 is connected to a charging connector (or other accessory port) on the handheld device, the scan engine 636 can communicate with the handheld device or with an application on the handheld device, such as an inventory or patient-safety application or other process control application on the handheld device. In this way, firmware or applications of the jacket 600 may communicate with data and/or applications stored on the handheld device.

Figure 6J:
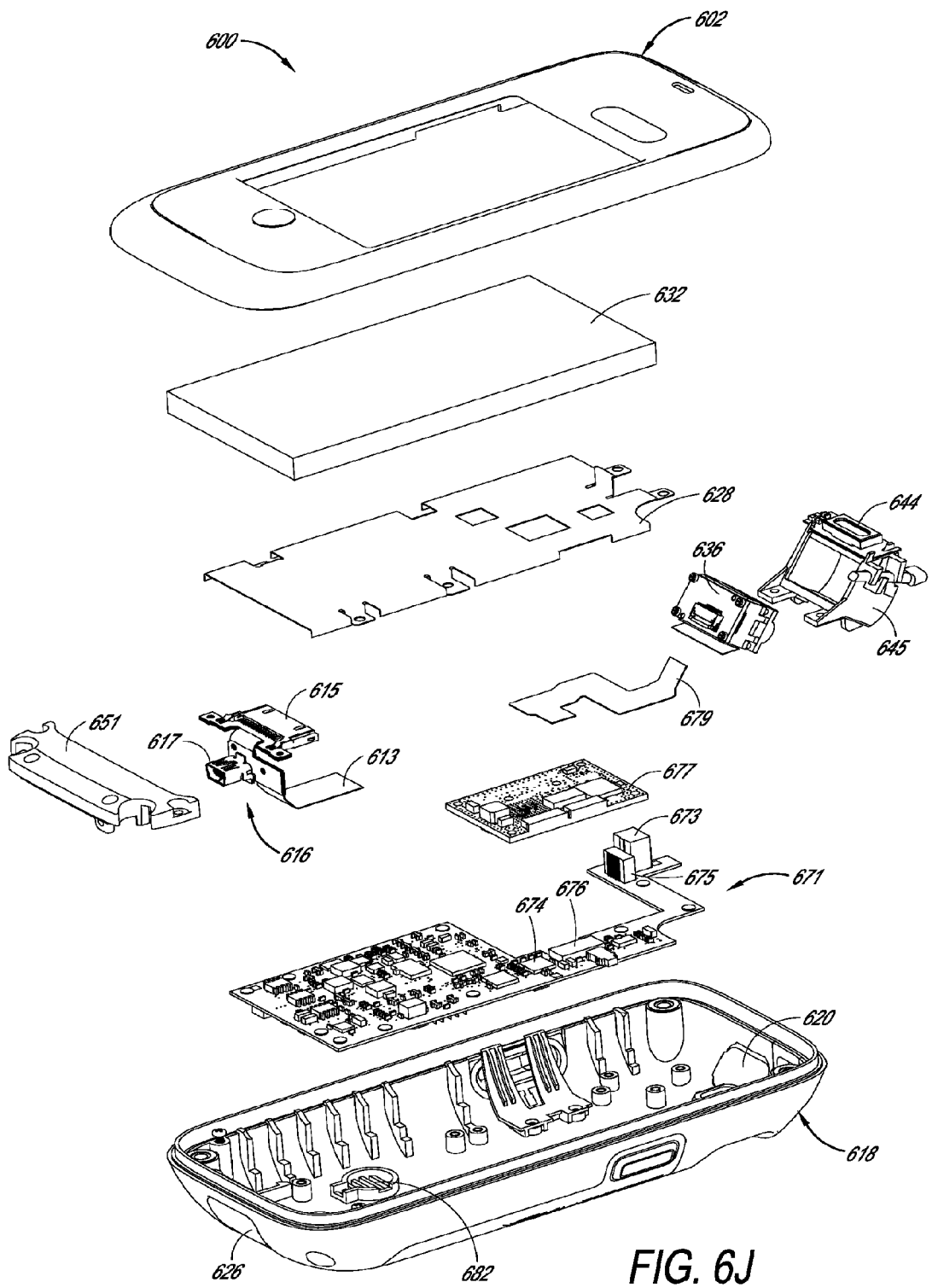
FIG. 6J shows an exploded view of the jacket 600 and its various components.

FIG. 6J shows an exploded view of the jacket 600 and its various components, including the front cover 602, the back cover 618, the battery 632, the shield 628, the scan engine 636, and the scanning window 620. As can be seen in FIG. 6J, the jacket 600 can a scanning engine bracket 645 and an optional speaker 644 disposed on the scanning engine bracket 645. The jacket 600 can also include one or more microphones such that the jacket 600 can be configured to allow use of a non-cellular handheld device as a VoIP handset in a healthcare setting.

As mentioned above, in some embodiments, the jacket 600 can include a scanner board 677 and a main circuit board 671. The main circuit board 671 can include a battery connector 673, a scanning engine connector 675, a scanner board connection 676, and a scan button connection 674. The main circuit board 671 may also be connected with an input port 617 and/or connector 615 of the connector assembly 616 via a cable 613 extending between the connector assembly 616 and the main circuit board. In some embodiments, the scanner board 677 can be connected to the scanning engine 636 via a flexible cable 679 routed therebetween. The jacket 600 can also include a vibrating element 682 disposed in the bottom cover 618 and electrically connected to the main circuit board 671. In this way, the main circuit board 671 can centralize the inputs and outputs of various electronic structures which may be housed within the jacket 600. In some embodiments, the jacket 600 can also include a bracket structure 651 configured to position internal components of the jacket 600 (for example, the battery 632 or shield 628) relative to the front cover 602 and back cover 618.

Still referring to FIG. 6J, in some embodiments the front cover 602 can include one or more compressible gaskets disposed on an underside of the front cover around the opening 611. In this way, the front cover 602 and the one or more gaskets can circumferentially engage or contact at least a portion of an outer surface handheld device (for example, an upper surface or screen) disposed within the jacket 600. As a result, the contact or engagement between the front cover 602 and the handheld device can be configured to provide a seal or boundary for the portion of the receiving area 606 disposed below the outer surface of the handheld device that is exposed through the opening 611. Thus, the receiving area 606 can be sealed or otherwise protected from liquids (water, blood, bodily fluids, medications, cleaning agents, etc.) and/or solid particles (medical powders, dust, dirt, debris, etc.) that the jacket 600 may be exposed to during use.

As discussed above, even though the portion of the receiving area 606 disposed below the outer surface of the handheld device may be sealed by the front cover 602 and outer surface of the handheld device, the outer surface of the handheld device may be directly contacted through the opening 611. In other words, the jacket 600 does not require a screen to be disposed over the handheld device to seal internal electrical components of a handheld terminal formed by the jacket 600 and the handheld device. In some instances, forming a seal between the jacket 600 and handheld device while allowing an input surface of the handheld device to be directly contactable can improve input sensitivity of the handheld device as compared with embodiments that utilize a separate screen over the handheld device. In some embodiments, the one or more compressible gaskets may be sized and/or shaped to absorb impactful forces on the jacket 600 to limit the transfer of these forces to the handheld device.

In some embodiments, the seal for the portion of the receiving area 606 disposed below the outer surface of the handheld device can be configured to meet an ingress protection rating or international protection rating required or preferred for a particular use. For example, the jacket 600 can be configured to provide an "IP54" protection rating for the internal electrical components (including internal components of the handheld device). Of course, the jacket 600 can be configured to provide more, or less, protection against the intrusion of solid particles and liquids. In some embodiments, the front and back covers 602, 618 can be covered or coated with a drop-resistant (for example, compressible) and liquid-proof or liquid resistant material, and can be provided with an interengaging structure configured to create a seal to prevent the ingress of water and cleaning fluids. In this way, the front and back covers 602, 618 can provide another seal to protect internal components housed within the jacket 600.

The foregoing description details certain embodiments of the invention. It will be appreciated, however, that no matter how detailed the foregoing appears in text, the invention can be practiced in many ways. For example, although described herein within the context of a jacket designed for use with a non-cellular handheld device, it will be understood by those skilled in the art that these techniques and systems may be extended beyond the specifically disclosed embodiments to other embodiments and/or uses and obvious modifications and equivalents thereof, including, for example, use with cellular and other types of handheld devices. It will also be appreciated that the above-described system can be implemented in additional environments and is not limited to the healthcare setting. For example, the system may be implemented in many other industries and environments that involve inventory identification and/or tracking, especially where a mobile inventory identification and/or tracking system may be desirable. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the systems disclosed herein should not be limited by the particular disclosed embodiments described above.

Further, it will be appreciated by those skilled in the art that various modifications and changes may be made without departing from the scope of the present disclosure. The drawings and the detailed description of certain inventive embodiments given so far are only illustrative, and they are only used to describe certain inventive embodiments, and should not be considered to limit the meaning or restrict the range of the present disclosure described in the claims. Indeed, it will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. Therefore, it will be appreciated to those skilled in the art that various modifications may be made and other equivalent embodiments are available. The scope of the invention should therefore be construed in accordance with the appended claims and any equivalents thereof.

What is claimed is:

1. An apparatus, comprising:
   a jacket including: a first portion defining a scan window, and a second portion opposite the first portion defining a viewing window, the viewing window defining a plane, the jacket defining a plurality of receiving areas; and
   a scan engine disposed in a first receiving area from the plurality of receiving areas and aligned with the scan window to define an optical path, the scan engine configured to decode a barcode in the optical path into a format compatible with a handheld device, the scan engine movable to define an angle of the optical path with respect to the plane,
   a second receiving area from the plurality of receiving areas configured to receive the handheld device.

2. The apparatus of claim 1, wherein the angle is between 70 degrees and 90 degrees.

3. The apparatus of claim 1, further comprising a speaker configured to communicate with the handheld device when the handheld device is received in the second receiving area.

4. The apparatus of claim 1, further comprising a microphone configured to communicate with the handheld device when the handheld device is received in the second receiving area.

5. The apparatus of claim 1, further comprising a vibrating element configured to communicate with the handheld device when the handheld device is received in the second receiving area.

6. The apparatus of claim 1, further comprising a pass-through button configured to align with an input button of the handheld device when the handheld device is received in the second receiving area.

7. The apparatus of claim 1, wherein the second portion further defines a transparent window configured to align with a camera of the handheld device when the handheld device is received in the second receiving area.

8. An apparatus, comprising:
    a jacket including: a first portion defining a scan window, and a second portion defining a viewing window, the viewing window defining a plane;
    the jacket defining a plurality of receiving areas; and
    a scan engine disposed in a first receiving area from the plurality of receiving areas and aligned with the scan window to define an optical path, the scan engine configured to decode a barcode into a format compatible with a handheld device, the optical path disposed at an angle with respect to a direction that is normal to the plane,
    a second receiving area from the plurality of receiving areas configured to receive the handheld device.

9. The apparatus of claim 8, wherein the angle is between 5 degrees and 15 degrees.

10. The apparatus of claim 8, further comprising a microphone configured to communicate with the handheld device when the handheld device is received in the second receiving area.

11. The apparatus of claim 8, further comprising a vibrating element configured to communicate with the handheld device when the handheld device is received in the second receiving area.

12. The apparatus of claim 8, wherein the second portion further defines a transparent window configured to align with a camera of the handheld device when the handheld device is received in the second receiving area.

13. An apparatus, comprising:
    a jacket including: a first portion defining a scan window, and a second portion opposite the first portion defining a viewing window, the viewing window defining a plane, the jacket defining a plurality of receiving areas;
    a scan engine disposed in a first receiving area from the plurality of receiving areas and aligned with the scan window to define an optical path, the scan engine not configured to decode a barcode, the scan engine movable to define an angle of the optical path with respect to the plane; and
    conversion circuitry disposed in a second receiving area from the plurality of receiving areas, the conversion circuitry configured to receive a signal associated with the barcode, and convert the signal associated with the barcode into a format for processing at a microcontroller such that the microcontroller decodes the barcode into a format that is readable by a handheld device,
    a third receiving area from the plurality of receiving areas configured to receive the handheld device.

14. The apparatus of claim 13, wherein the angle is between 70 degrees and 90 degrees.

15. The apparatus of claim 13, further comprising a microphone configured to communicate with the handheld device when the handheld device is received in the second receiving area.

16. The apparatus of claim 13, further comprising a vibrating element configured to communicate with the handheld device when the handheld device is received in the second receiving area.

17. The apparatus of claim 13, wherein the second portion further defines a transparent window configured to align with a camera of the handheld device when the handheld device is received in the second receiving area.

* * * * *